(12) United States Patent
Miller

(10) Patent No.: US 9,717,601 B2
(45) Date of Patent: Aug. 1, 2017

(54) EXPANDABLE INTERVERTEBRAL IMPLANT, SYSTEM, KIT AND METHOD

(71) Applicant: DePuy Synthes Products, Inc., Raynham, MA (US)

(72) Inventor: William Miller, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 642 days.

(21) Appl. No.: 13/780,796

(22) Filed: Feb. 28, 2013

(65) Prior Publication Data

US 2014/0243982 A1 Aug. 28, 2014

(51) Int. Cl.
  *A61F 2/44* (2006.01)
  *A61F 2/46* (2006.01)
  *A61F 2/30* (2006.01)

(52) U.S. Cl.
  CPC .......... *A61F 2/4455* (2013.01); *A61F 2/447* (2013.01); *A61F 2/4611* (2013.01); *A61F 2/4684* (2013.01); *A61F 2002/3008* (2013.01); *A61F 2002/3082* (2013.01); *A61F 2002/3083* (2013.01); *A61F 2002/30131* (2013.01); *A61F 2002/30156* (2013.01); *A61F 2002/30158* (2013.01); *A61F 2002/30281* (2013.01); *A61F 2002/30398* (2013.01); *A61F 2002/30411* (2013.01); *A61F 2002/30556* (2013.01); *A61F 2002/30579* (2013.01); *A61F 2002/30772* (2013.01); *A61F 2002/30774* (2013.01);
  (Continued)

(58) Field of Classification Search
  None
  See application file for complete search history.

(56) References Cited

U.S. PATENT DOCUMENTS 3,867,728 A 2/1975 Stubstad et al.
4,349,921 A 9/1982 Kuntz
(Continued)

FOREIGN PATENT DOCUMENTS

CN 101909548 A 12/2010
DE 2804936 8/1979
(Continued)

OTHER PUBLICATIONS

International Patent Application No. PCT/US2013/029014, International Search Report dated Jul. 1, 2013, 7 pages.
(Continued)

*Primary Examiner* — Sameh Boles
(74) *Attorney, Agent, or Firm* — Baker & Hostetler LLP

(57) ABSTRACT

An implant includes a first plate and a second plate, a first wedge member and a second wedge member spaced from the first wedge member that couple the first and second plates together. The first and second wedge members configured to translate along the first and second plates from a first contracted configuration into a second separated configuration. The implant includes an actuation member coupled to the first wedge member and the second wedge member. The actuating member defines a flange extending toward the first and second plates. The actuation member configured to move the first and second wedge members from the first contracted configuration into the second separated configuration so that the first and second plates separate from each other.

27 Claims, 14 Drawing Sheets

(52) U.S. Cl.
CPC .......... *A61F 2002/30828* (2013.01); *A61F 2002/30836* (2013.01); *A61F 2002/30904* (2013.01); *A61F 2002/4623* (2013.01); *A61F 2002/4627* (2013.01)

(56) References Cited

U.S. PATENT DOCUMENTS

| | | |
|---|---|---|
| 4,743,256 A | 5/1988 | Brantigan |
| 4,759,766 A | 7/1988 | Buettner-Janz et al. |
| 4,863,476 A | 9/1989 | Shepperd |
| 4,871,366 A | 10/1989 | von Recum et al. |
| 4,878,915 A | 11/1989 | Brantigan |
| 5,059,193 A | 10/1991 | Kuslich |
| 5,071,437 A | 12/1991 | Steffee |
| 5,123,926 A | 6/1992 | Pisharodi |
| 5,290,312 A | 3/1994 | Kojimoto et al. |
| 5,314,477 A | 5/1994 | Marnay |
| 5,344,252 A | 9/1994 | Kakimoto |
| 5,370,697 A | 12/1994 | Baumgartner |
| 5,390,683 A | 2/1995 | Pisharodi |
| 5,401,269 A | 3/1995 | Buttner-Janz et al. |
| 5,425,773 A | 6/1995 | Boyd et al. |
| 5,443,514 A | 8/1995 | Steffee |
| 5,507,816 A | 4/1996 | Bullivant |
| 5,522,899 A | 6/1996 | Michelson |
| 5,534,029 A | 7/1996 | Shima |
| 5,554,191 A | 9/1996 | Lahille et al. |
| 5,556,431 A | 9/1996 | Buttner-Janz |
| 5,562,738 A | 10/1996 | Boyd et al. |
| 5,609,635 A | 3/1997 | Michelson |
| 5,653,763 A | 8/1997 | Errico et al. |
| 5,658,335 A | 8/1997 | Allen |
| 5,665,122 A | 9/1997 | Kambin |
| 5,676,701 A | 10/1997 | Yuan et al. |
| 5,683,465 A | 11/1997 | Shinn et al. |
| 5,697,977 A | 12/1997 | Pisharodi |
| 5,716,415 A | 2/1998 | Steffee |
| 5,772,661 A | 6/1998 | Michelson |
| 5,782,832 A | 7/1998 | Larsen et al. |
| 5,797,909 A | 8/1998 | Michelson |
| 5,860,973 A | 1/1999 | Michelson |
| 5,865,848 A | 2/1999 | Baker |
| 5,888,224 A | 3/1999 | Beckers et al. |
| 5,888,226 A | 3/1999 | Rogozinski |
| 5,888,227 A | 3/1999 | Cottle |
| 5,893,889 A | 4/1999 | Harrington |
| 5,893,890 A | 4/1999 | Pisharodi |
| 5,980,522 A | 11/1999 | Koros et al. |
| 5,989,291 A | 11/1999 | Ralph et al. |
| 6,039,761 A | 3/2000 | Li |
| 6,039,763 A | 3/2000 | Shelokov |
| 6,045,579 A | 4/2000 | Hochshuler |
| 6,080,155 A | 6/2000 | Michelson |
| 6,096,038 A | 8/2000 | Michelson |
| 6,102,950 A | 8/2000 | Vaccaro |
| 6,106,557 A | 8/2000 | Robioneck et al. |
| 6,113,637 A | 9/2000 | Gill et al. |
| 6,113,638 A | 9/2000 | Williams et al. |
| 6,117,174 A | 9/2000 | Nolan |
| 6,127,597 A | 10/2000 | Beyar et al. |
| 6,129,763 A | 10/2000 | Chauvin et al. |
| 6,146,387 A | 11/2000 | Trott et al. |
| 6,176,882 B1 | 1/2001 | Biedermann et al. |
| 6,179,794 B1 | 1/2001 | Burras |
| 6,179,873 B1 | 1/2001 | Zientek |
| 6,183,517 B1 | 2/2001 | Suddaby |
| 6,193,757 B1 | 2/2001 | Foley et al. |
| 6,296,647 B1 | 10/2001 | Robioneck et al. |
| 6,302,914 B1 | 10/2001 | Michelson |
| 6,332,895 B1 | 12/2001 | Suddaby |
| 6,368,350 B1 | 4/2002 | Erickson et al. |
| 6,368,351 B1 | 4/2002 | Glenn |
| 6,375,682 B1 | 4/2002 | Fleischmann et al. |
| 6,387,130 B1 | 5/2002 | Stone |
| 6,409,766 B1 | 6/2002 | Brett |
| 6,419,705 B1 | 7/2002 | Erickson |
| 6,419,706 B1 | 7/2002 | Graf |
| 6,436,140 B1 | 8/2002 | Liu et al. |
| 6,454,806 B1 | 9/2002 | Cohen et al. |
| 6,454,807 B1 | 9/2002 | Jackson |
| 6,468,310 B1 | 10/2002 | Ralph et al. |
| 6,488,710 B2 | 12/2002 | Besselink |
| 6,517,580 B1 | 2/2003 | Ramadan et al. |
| 6,527,804 B1 | 3/2003 | Gauchet et al. |
| 6,533,818 B1 | 3/2003 | Weber et al. |
| 6,558,424 B2 | 5/2003 | Thalgott |
| 6,562,074 B2 | 5/2003 | Gerbec et al. |
| 6,582,468 B1 | 6/2003 | Gauchet |
| 6,610,094 B2 | 8/2003 | Husson |
| 6,641,614 B1 | 11/2003 | Wagner et al. |
| 6,648,917 B2 | 11/2003 | Gerbec et al. |
| 6,669,732 B2 | 12/2003 | Serhan et al. |
| 6,676,665 B2 | 1/2004 | Foley et al. |
| 6,706,070 B1 | 3/2004 | Wagner et al. |
| 6,719,796 B2 | 4/2004 | Cohen et al. |
| 6,723,126 B1 | 4/2004 | Berry |
| 6,733,532 B1 | 5/2004 | Gauchet et al. |
| 6,740,117 B2 | 5/2004 | Ralph et al. |
| 6,743,255 B2 | 6/2004 | Ferree |
| 6,793,678 B2 | 9/2004 | Hawkins |
| 6,805,714 B2 | 10/2004 | Sutcliffe |
| 6,824,565 B2 | 11/2004 | Muhanna |
| 6,852,129 B2 | 2/2005 | Gerbec et al. |
| 6,855,167 B2 | 2/2005 | Shimp |
| 6,863,673 B2 | 3/2005 | Gerbec et al. |
| 6,881,229 B2 | 4/2005 | Khandkar et al. |
| 6,893,464 B2 | 5/2005 | Kiester |
| 6,936,071 B1 | 8/2005 | Marnay et al. |
| 6,953,477 B2 | 10/2005 | Berry |
| 6,955,691 B2 | 10/2005 | Chae et al. |
| 6,969,404 B2 | 11/2005 | Ferree |
| 6,969,405 B2 | 11/2005 | Suddaby |
| 7,008,431 B2 | 3/2006 | Simonson |
| 7,018,412 B2 | 3/2006 | Ferreira et al. |
| 7,018,416 B2 | 3/2006 | Hanson et al. |
| 7,037,339 B2 | 5/2006 | Houfburg et al. |
| 7,083,650 B2 | 8/2006 | Moskowitz et al. |
| 7,094,257 B2 | 8/2006 | Mujwid et al. |
| 7,156,876 B2 | 1/2007 | Moumene et al. |
| 7,211,112 B2 | 5/2007 | Baynham et al. |
| 7,217,293 B2 | 5/2007 | Branch |
| 7,220,280 B2 | 5/2007 | Kast et al. |
| 7,223,292 B2 | 5/2007 | Messerli et al. |
| 7,226,483 B2 | 6/2007 | Gerber et al. |
| 7,235,101 B2 | 6/2007 | Berry et al. |
| 7,300,440 B2 | 11/2007 | Zdeblick |
| 7,326,248 B2 | 2/2008 | Michelson |
| 7,445,636 B2 | 11/2008 | Michelson |
| 7,503,933 B2 | 3/2009 | Michelson |
| 7,507,241 B2 | 3/2009 | Levy et al. |
| 7,517,363 B2 | 4/2009 | Rogers |
| 7,569,054 B2 | 8/2009 | Michelson |
| 7,569,074 B2 | 8/2009 | Eisermann et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,691,147 B2 | 4/2010 | Gutlin et al. |
| 7,703,727 B2 | 4/2010 | Selness |
| 7,722,612 B2 | 5/2010 | Sala et al. |
| 7,722,674 B1 | 5/2010 | Grotz |
| 7,749,270 B2 | 7/2010 | Peterman |
| 7,771,473 B2 | 8/2010 | Thramann |
| 7,785,368 B2 | 8/2010 | Schaller |
| 7,789,914 B2 | 9/2010 | Michelson |
| 7,799,083 B2 | 9/2010 | Smith et al. |
| 7,819,921 B2 | 10/2010 | Grotz |
| 7,824,445 B2 | 11/2010 | Biro et al. |
| 7,837,734 B2 | 11/2010 | Zucherman et al. |
| 7,846,206 B2 | 12/2010 | Oglaza et al. |
| 7,850,733 B2 | 12/2010 | Baynham et al. |
| 7,854,766 B2 | 12/2010 | Moskowitz et al. |
| 7,857,840 B2 | 12/2010 | Krebs |
| 7,874,980 B2 | 1/2011 | Sonnenschein et al. |
| 7,879,098 B1 | 2/2011 | Simmons |

(56) References Cited

U.S. PATENT DOCUMENTS

| | | |
|---|---|---|
| 7,887,589 B2 | 2/2011 | Glenn et al. |
| 7,909,870 B2 | 3/2011 | Kraus |
| 7,922,729 B2 | 4/2011 | Michelson |
| 7,951,199 B2 | 5/2011 | Miller |
| 7,985,231 B2 | 7/2011 | Sankaran |
| 7,993,403 B2 | 8/2011 | Foley et al. |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,043,381 B2 | 10/2011 | Hestad et al. |
| 8,062,375 B2 | 11/2011 | Glerum et al. |
| 8,075,621 B2 | 12/2011 | Michelson |
| 8,105,382 B2 | 1/2012 | Olmos et al. |
| 8,114,088 B2 | 2/2012 | Miller |
| 8,177,812 B2 | 5/2012 | Sankaran |
| 8,192,495 B2 | 6/2012 | Simpson et al. |
| 8,221,501 B2 | 7/2012 | Eisermann et al. |
| 8,221,502 B2 | 7/2012 | Branch |
| 8,231,681 B2 | 7/2012 | Castleman et al. |
| 8,236,058 B2 | 8/2012 | Fabian et al. |
| 8,241,358 B2 | 8/2012 | Butler et al. |
| 8,257,442 B2 | 9/2012 | Edie et al. |
| 8,262,666 B2 | 9/2012 | Baynham et al. |
| 8,267,939 B2 | 9/2012 | Cipoletti et al. |
| 8,273,128 B2 | 9/2012 | Oh et al. |
| 8,287,599 B2 | 10/2012 | McGuckin |
| 8,303,663 B2 | 11/2012 | Jimenez et al. |
| 8,323,345 B2 | 12/2012 | Sledge |
| 8,328,852 B2 | 12/2012 | Zehavi et al. |
| 8,337,559 B2 | 12/2012 | Hansell et al. |
| 8,353,961 B2 | 1/2013 | McClintock et al. |
| 8,382,842 B2 | 2/2013 | Greenhalgh et al. |
| 8,398,713 B2 | 3/2013 | Weiman |
| 8,403,990 B2 | 3/2013 | Dryer et al. |
| 8,409,291 B2 | 4/2013 | Blackwell et al. |
| 8,435,298 B2 | 5/2013 | Weiman |
| 8,454,617 B2 | 6/2013 | Schaller |
| 8,486,148 B2 | 7/2013 | Butler et al. |
| 8,491,657 B2 | 7/2013 | Attia et al. |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim |
| 8,591,585 B2 | 11/2013 | McLaughlin et al. |
| 8,603,170 B2 | 12/2013 | Cipoletti et al. |
| 8,623,091 B2 | 1/2014 | Suedkamp et al. |
| 8,628,576 B2 | 1/2014 | Triplett et al. |
| 8,628,578 B2 | 1/2014 | Miller et al. |
| 8,632,595 B2 | 1/2014 | Weiman |
| 8,663,329 B2 | 3/2014 | Ernst |
| 8,668,740 B2 | 3/2014 | Rhoda et al. |
| 8,679,183 B2 | 3/2014 | Glerum et al. |
| 8,685,098 B2 | 4/2014 | Glerum et al. |
| 8,696,751 B2 | 4/2014 | Ashley et al. |
| 8,709,086 B2 | 4/2014 | Glerum et al. |
| 8,715,351 B1 | 5/2014 | Pinto |
| 8,721,723 B2 | 5/2014 | Hansell et al. |
| 8,753,398 B2 | 6/2014 | Gordon et al. |
| 8,771,360 B2 | 7/2014 | Jimenez et al. |
| 8,778,025 B2 | 7/2014 | Ragab et al. |
| 8,795,366 B2 | 8/2014 | Varela |
| 8,828,085 B1 | 9/2014 | Jensen |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,307 B2 | 12/2014 | Hawkins et al. |
| 8,926,704 B2 | 1/2015 | Glerum |
| 8,936,641 B2 | 1/2015 | Cain |
| 8,940,052 B2 | 1/2015 | Lechmann et al. |
| 8,979,860 B2 | 3/2015 | Voellmicke et al. |
| 8,986,387 B1 | 3/2015 | To et al. |
| 9,005,291 B2 | 4/2015 | Loebl et al. |
| 9,039,767 B2 | 5/2015 | Raymond et al. |
| 9,039,771 B2 | 5/2015 | Glerum et al. |
| 9,060,876 B1 | 6/2015 | To et al. |
| 9,078,767 B1 | 7/2015 | McLean |
| 9,095,446 B2 | 8/2015 | Landry et al. |
| 9,095,447 B2 | 8/2015 | Barreiro et al. |
| 9,101,488 B2 | 8/2015 | Malandain |
| 9,101,489 B2 | 8/2015 | Protopsaltis et al. |
| 9,107,766 B1 | 8/2015 | Mclean et al. |
| 2002/0010070 A1 | 1/2002 | Cales et al. |
| 2002/0068976 A1 | 6/2002 | Jackson |
| 2002/0068977 A1 | 6/2002 | Jackson |
| 2002/0128715 A1 | 9/2002 | Bryan et al. |
| 2002/0128716 A1 | 9/2002 | Cohen et al. |
| 2002/0138146 A1 | 9/2002 | Jackson |
| 2002/0151976 A1 | 10/2002 | Foley et al. |
| 2002/0165612 A1 | 11/2002 | Gerber et al. |
| 2003/0004575 A1 | 1/2003 | Erickson |
| 2003/0004576 A1 | 1/2003 | Thalgott |
| 2003/0023305 A1 | 1/2003 | McKay |
| 2003/0040799 A1 | 2/2003 | Boyd et al. |
| 2003/0065396 A1 | 4/2003 | Michelson |
| 2003/0078667 A1 | 4/2003 | Manasas et al. |
| 2003/0130739 A1 | 7/2003 | Gerbec et al. |
| 2003/0135275 A1 | 7/2003 | Garcia |
| 2003/0139812 A1 | 7/2003 | Garcia |
| 2003/0139813 A1 | 7/2003 | Messerli et al. |
| 2003/0204261 A1 | 10/2003 | Eiserman |
| 2003/0233145 A1 | 12/2003 | Landry et al. |
| 2004/0030387 A1 | 2/2004 | Landry et al. |
| 2004/0064144 A1 | 4/2004 | Johnson et al. |
| 2004/0087947 A1 | 5/2004 | Lim et al. |
| 2004/0088055 A1 | 5/2004 | Hanson et al. |
| 2004/0127991 A1 | 7/2004 | Ferree |
| 2004/0153065 A1 | 8/2004 | Lim |
| 2004/0153156 A1 | 8/2004 | Cohen et al. |
| 2004/0162618 A1 | 8/2004 | Mujwid et al. |
| 2004/0172133 A1 | 9/2004 | Gerber et al. |
| 2004/0172134 A1 | 9/2004 | Berry |
| 2004/0186570 A1 | 9/2004 | Rapp |
| 2004/0186577 A1 | 9/2004 | Ferree |
| 2004/0230309 A1 | 11/2004 | DiMauro |
| 2005/0019365 A1 | 1/2005 | Frauchiger et al. |
| 2005/0038515 A1 | 2/2005 | Kunzler |
| 2005/0113916 A1 | 5/2005 | Branch |
| 2005/0113917 A1 | 5/2005 | Chae et al. |
| 2005/0125062 A1 | 6/2005 | Biedermann et al. |
| 2005/0165485 A1 | 7/2005 | Trieu |
| 2005/0222681 A1 | 10/2005 | Richley et al. |
| 2005/0256576 A1 | 11/2005 | Moskowitz et al. |
| 2005/0261769 A1 | 11/2005 | Moskowitz et al. |
| 2005/0278026 A1 | 12/2005 | Gordon et al. |
| 2006/0058876 A1 | 3/2006 | McKinley |
| 2006/0058880 A1 | 3/2006 | Wysocki |
| 2006/0100706 A1 | 5/2006 | Shadduck et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0136062 A1 | 6/2006 | DiNello et al. |
| 2006/0142858 A1 | 6/2006 | Colleran et al. |
| 2006/0206207 A1 | 9/2006 | Dryer et al. |
| 2006/0235531 A1 | 10/2006 | Buettner |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2007/0010886 A1 | 1/2007 | Banick et al. |
| 2007/0055377 A1 | 3/2007 | Hanson et al. |
| 2007/0118222 A1 | 5/2007 | Lang |
| 2007/0149978 A1 | 6/2007 | Shezifi et al. |
| 2007/0173939 A1 | 7/2007 | Kim et al. |
| 2007/0173940 A1 | 7/2007 | Hestad et al. |
| 2007/0178222 A1 | 8/2007 | Storey et al. |

(56) References Cited

U.S. PATENT DOCUMENTS

| | | |
|---|---|---|
| 2007/0191959 A1 | 8/2007 | Hartmann et al. |
| 2007/0198089 A1 | 8/2007 | Moskowitz et al. |
| 2007/0208423 A1 | 9/2007 | Messerli et al. |
| 2007/0219634 A1 | 9/2007 | Greenhalgh et al. |
| 2007/0233244 A1 | 10/2007 | Lopez et al. |
| 2007/0270968 A1 | 11/2007 | Baynham et al. |
| 2007/0276375 A1 | 11/2007 | Rapp |
| 2007/0299521 A1 | 12/2007 | Glenn |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0058944 A1 | 3/2008 | Duplessis et al. |
| 2008/0065219 A1 | 3/2008 | Dye |
| 2008/0082173 A1 | 4/2008 | Delurio et al. |
| 2008/0132934 A1 | 6/2008 | Reiley |
| 2008/0140207 A1 | 6/2008 | Olmos et al. |
| 2008/0147193 A1 | 6/2008 | Matthis et al. |
| 2008/0154377 A1 | 6/2008 | Voellmicke et al. |
| 2008/0161927 A1 | 7/2008 | Savage |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0195209 A1 | 8/2008 | Garcia et al. |
| 2008/0243251 A1 | 10/2008 | Stad et al. |
| 2008/0243254 A1 | 10/2008 | Butler |
| 2008/0249622 A1 | 10/2008 | Gray |
| 2008/0281425 A1 | 11/2008 | Thalgott |
| 2009/0005873 A1 | 1/2009 | Slivka et al. |
| 2009/0030423 A1 | 1/2009 | Puno |
| 2009/0054991 A1 | 2/2009 | Biyani et al. |
| 2009/0076610 A1 | 3/2009 | Afzal |
| 2009/0099568 A1 | 4/2009 | Lowry et al. |
| 2009/0105712 A1 | 4/2009 | Dauster |
| 2009/0112320 A1 | 4/2009 | Kraus |
| 2009/0112324 A1 | 4/2009 | Refai et al. |
| 2009/0164020 A1 | 6/2009 | Janowski |
| 2009/0177284 A1 | 7/2009 | Rogers et al. |
| 2009/0198339 A1 | 8/2009 | Kleiner |
| 2009/0222096 A1 | 9/2009 | Trieu |
| 2009/0222099 A1 | 9/2009 | Liu et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0292361 A1 | 11/2009 | Lopez et al. |
| 2010/0016905 A1 | 1/2010 | Greenhalgh et al. |
| 2010/0076559 A1 | 3/2010 | Bagga |
| 2010/0114105 A1 | 5/2010 | Butters |
| 2010/0179594 A1 | 7/2010 | Theofilos et al. |
| 2010/0204795 A1 | 8/2010 | Greenhalgh |
| 2010/0234956 A1 | 9/2010 | Attia et al. |
| 2010/0262240 A1 | 10/2010 | Chavatte et al. |
| 2010/0286783 A1 | 11/2010 | Lechmann et al. |
| 2010/0324607 A1 | 12/2010 | Davis |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0093074 A1 | 4/2011 | Glerum et al. |
| 2011/0130835 A1 | 6/2011 | Ashley et al. |
| 2011/0130838 A1 | 6/2011 | Lopez |
| 2011/0144753 A1 | 6/2011 | Marchek et al. |
| 2011/0172716 A1 | 7/2011 | Glerum |
| 2011/0270261 A1 | 11/2011 | Mast et al. |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0185049 A1 | 7/2012 | Varela |
| 2012/0197403 A1 | 8/2012 | Merves |
| 2012/0197405 A1 | 8/2012 | Cuevas et al. |
| 2012/0226357 A1 | 9/2012 | Varela |
| 2012/0232552 A1 | 9/2012 | Morgenstern et al. |
| 2012/0265309 A1 | 10/2012 | Glerum et al. |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2013/0030536 A1 | 1/2013 | Rhoda et al. |
| 2013/0085572 A1 | 4/2013 | Glerum et al. |
| 2013/0085574 A1 | 4/2013 | Sledge |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1* | 8/2013 | Alheidt ............... A61F 2/4611 623/17.16 |
| 2013/0310939 A1 | 11/2013 | Fabian et al. |
| 2014/0025169 A1 | 1/2014 | Lechmann et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0114423 A1 | 4/2014 | Suedkamp et al. |
| 2014/0128977 A1 | 5/2014 | Glerum et al. |
| 2014/0135934 A1 | 5/2014 | Hansell et al. |
| 2014/0142706 A1 | 5/2014 | Hansell et al. |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0228959 A1 | 8/2014 | Niemiec et al. |
| 2014/0243981 A1 | 8/2014 | Davenport et al. |
| 2014/0243982 A1 | 8/2014 | Miller |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0277474 A1 | 9/2014 | Robinson et al. |
| 2014/0303731 A1 | 10/2014 | Glerum et al. |
| 2014/0303732 A1 | 10/2014 | Rhoda et al. |
| 2014/0324171 A1 | 10/2014 | Glerum et al. |
| 2015/0012097 A1 | 1/2015 | Ibarra et al. |
| 2015/0045894 A1 | 2/2015 | Hawkins et al. |
| 2015/0094812 A1 | 4/2015 | Cain |
| 2015/0094813 A1 | 4/2015 | Lechmann et al. |
| 2015/0112438 A1 | 4/2015 | McLean |
| 2015/0157470 A1 | 6/2015 | Voellmicke et al. |
| 2015/0182347 A1 | 7/2015 | Robinson |
| 2015/0216672 A1 | 8/2015 | Cain et al. |
| 2015/0250606 A1 | 9/2015 | Mclean |
| 2016/0045333 A1 | 2/2016 | Baynham |
| 2016/0242929 A1 | 8/2016 | Voellmicke et al. |
| 2016/0317317 A1 | 11/2016 | Marchek et al. |

FOREIGN PATENT DOCUMENTS

| | | |
|---|---|---|
| DE | 3911610 | 10/1990 |
| DE | 4012622 | 7/1997 |
| DE | 202008001079 | 3/2008 |
| EP | 282161 | 9/1988 |
| EP | 678489 | 10/1995 |
| EP | 1290985 | 3/2003 |
| EP | 1532949 | 5/2005 |

(56) References Cited

FOREIGN PATENT DOCUMENTS

| | | |
|---|---|---|
| EP | 1541096 | 6/2005 |
| EP | 1683593 | 7/2006 |
| EP | 1698305 B1 | 8/2007 |
| EP | 1843723 | 3/2010 |
| EP | 2368529 | 9/2011 |
| EP | 2237748 B1 | 9/2012 |
| EP | 2764851 | 8/2014 |
| FR | 2718635 | 10/1995 |
| FR | 2730159 | 8/1996 |
| FR | 2874814 | 3/2006 |
| JP | 2003-526457 | 9/2003 |
| JP | 2006-516456 | 7/2006 |
| JP | 2011-509766 A | 3/2011 |
| WO | WO 94/04100 | 3/1994 |
| WO | WO 95/31158 | 11/1995 |
| WO | WO 97/00054 | 1/1997 |
| WO | WO 99/53871 | 10/1999 |
| WO | WO 00/12033 | 3/2000 |
| WO | WO 00/53127 | 9/2000 |
| WO | WO 00/74605 | 12/2000 |
| WO | WO 01/01893 | 1/2001 |
| WO | WO 01/01895 | 1/2001 |
| WO | WO 01/17464 | 3/2001 |
| WO | WO 2005/112834 | 12/2005 |
| WO | WO 2006/047587 | 5/2006 |
| WO | WO 2006/058281 | 6/2006 |
| WO | WO 2006/065419 | 6/2006 |
| WO | WO 2006/081843 | 8/2006 |
| WO | WO 2007/009107 | 1/2007 |
| WO | WO 2007/028098 | 3/2007 |
| WO | WO 2007/048012 | 4/2007 |
| WO | WO 2008/044057 | 4/2008 |
| WO | WO 2009/064787 | 5/2009 |
| WO | WO 2009/092102 | 7/2009 |
| WO | WO 2009/124269 | 10/2009 |
| WO | WO 2009/143496 | 11/2009 |
| WO | WO 2010/068725 | 6/2010 |
| WO | WO 2010/148112 | 12/2010 |
| WO | WO 2011/142761 | 11/2011 |
| WO | WO 2012/009152 | 1/2012 |
| WO | WO 2012/089317 | 7/2012 |
| WO | WO 2012/135764 | 10/2012 |
| WO | WO 2013/006669 | 1/2013 |
| WO | WO 2013/023096 | 2/2013 |
| WO | WO 2013/025876 | 2/2013 |
| WO | WO 2013/043850 | 5/2013 |
| WO | WO 2013/062903 | 5/2013 |
| WO | WO 2013/082184 | 6/2013 |
| WO | WO 2013/158294 | 10/2013 |
| WO | WO 2013/173767 | 11/2013 |
| WO | WO 2013/184946 | 12/2013 |
| WO | WO 2014/018098 | 1/2014 |
| WO | WO 2014/026007 | 2/2014 |
| WO | WO 2014/035962 | 3/2014 |
| WO | WO 2014/088521 | 6/2014 |
| WO | WO 2014/116891 | 7/2014 |

OTHER PUBLICATIONS

Chiang, Biomechanical Comparison of Instrumented Posterior Lumbar Interbody Fusion with One or Two Cages by Finite Element Analysis, Spine, 2006, pp. E682-E689, vol. 31(19), Lippincott Williams & Wilkins, Inc.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Gore, Technique of Cervical Interbody Fusion, Clinical Orthopaedics and Related Research, 1984, pp. 191-195, No. 188.
Hunt, Expanable cage placement via a posterolateral approach in lumbar spine reconstructions, Journal of Neurosurgery: Spine, 2006, pp. 271-274, vol. 5.
Krbec, [Replacement of the vertebral body with an expansion implant (Synex)], Acta Chir Orthop Traumatol Cech, 2002, pp. 158-162, vol. 69(3).
Polikeit, The importance of the endplate for interbody cages in the lumbar spine, Eur Spine J, 2003, pp. 556-561, vol. 12.
Shin, Posterior Lumbar Interbody Fusion via a Unilateral Approach, Yonsei Medical Journal, 2006, pp. 319-325, vol. 47(3).
Hoogland, T. et al., Total Lumbar Intervertebral Disc Replacement: testing of a New Articulating Space in Human Cadaver Spines—24 1 Annual ORS, Dallas TX, Feb. 21-23, 1978, 8 pages.
Spine Solutions Brochure—Prodisc 2001, 16 pages.
Link SB Charite Brochure—Intervertebral Prosthesis 1988, 29 pages.

* cited by examiner

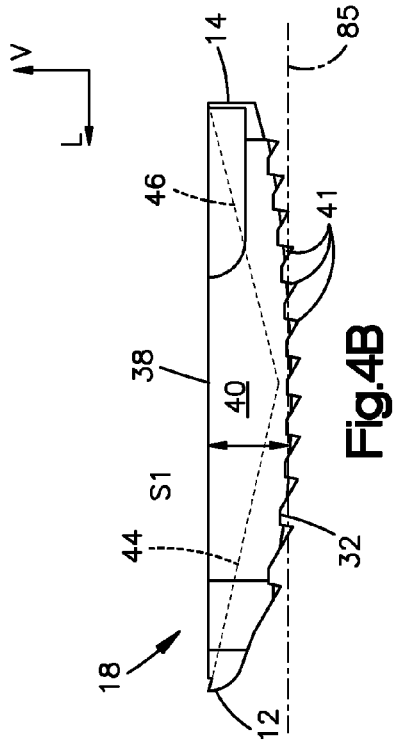
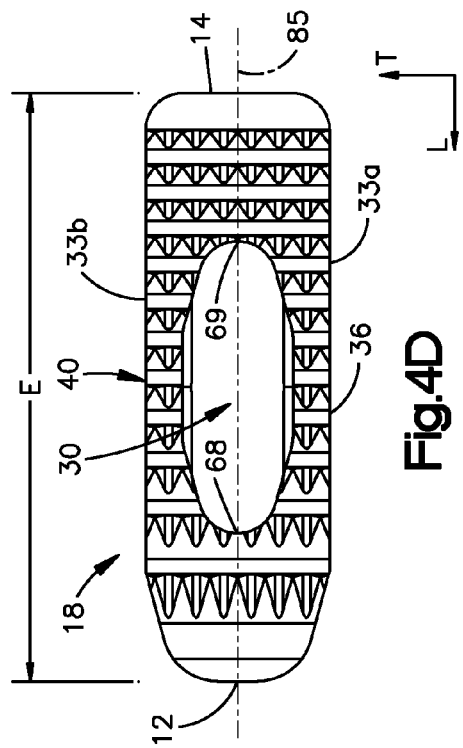
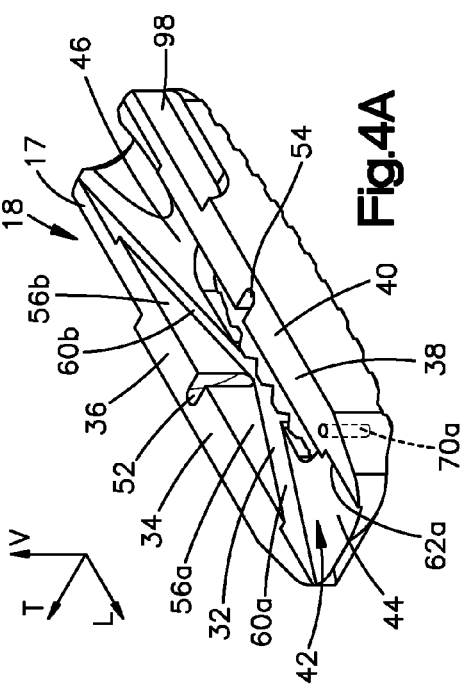
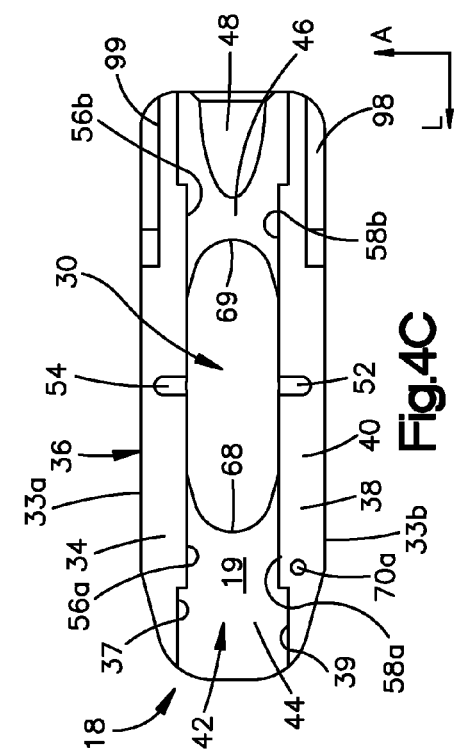

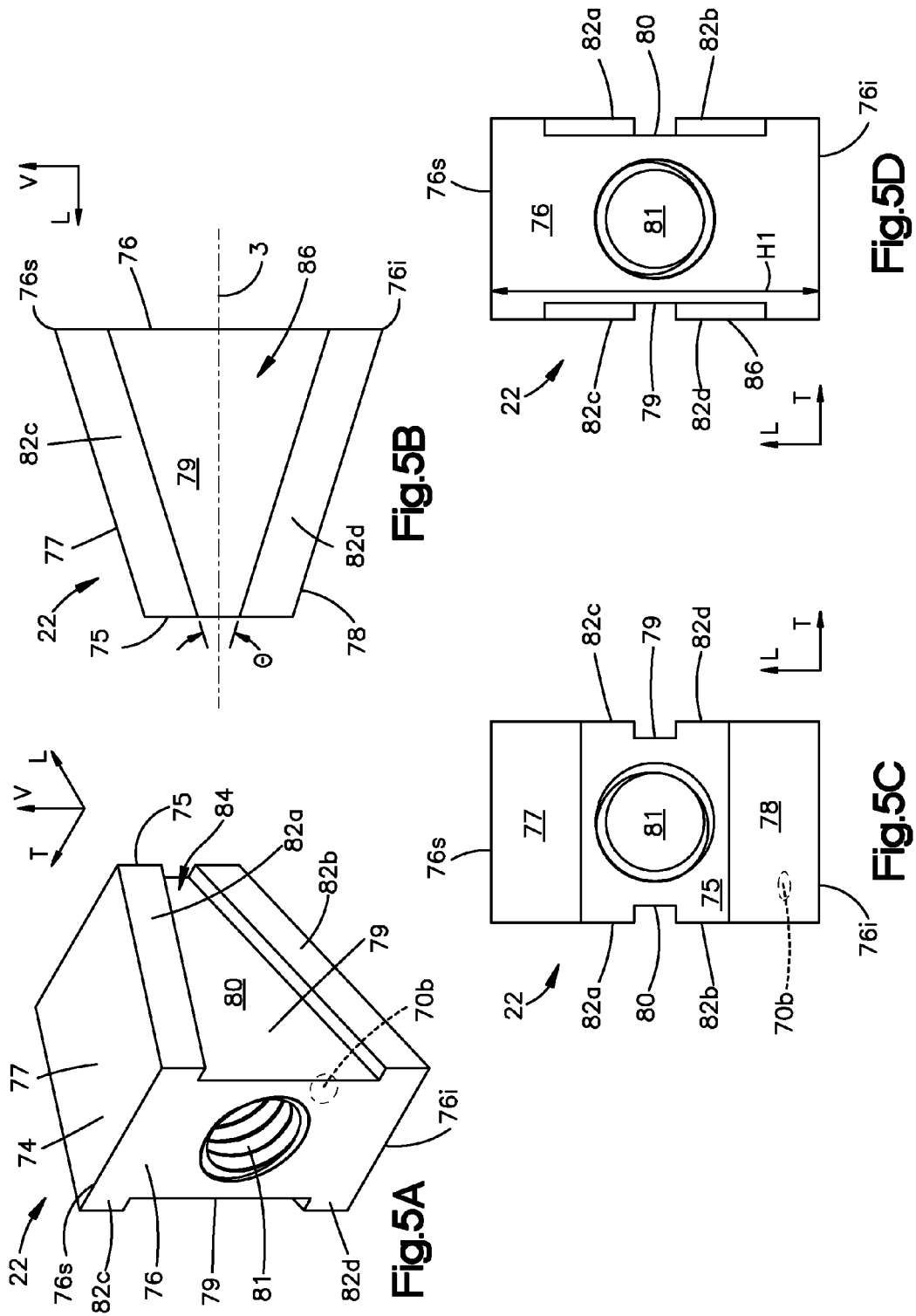

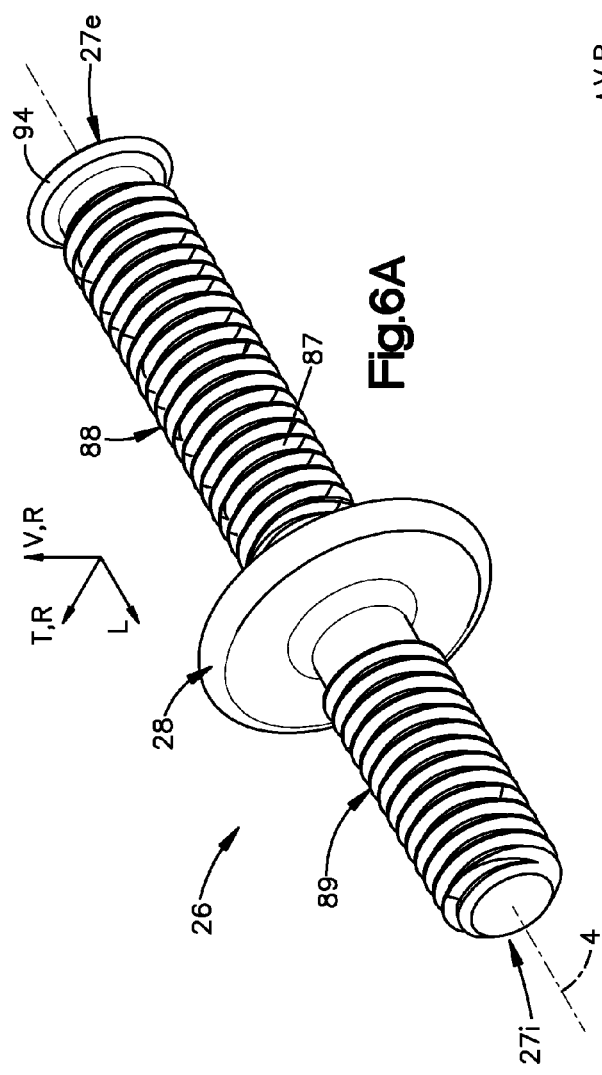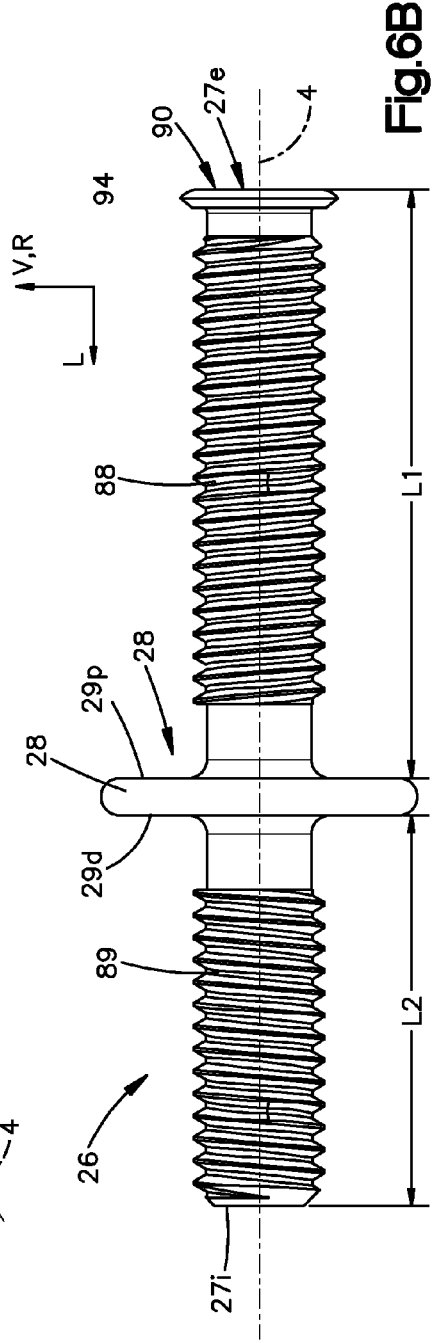

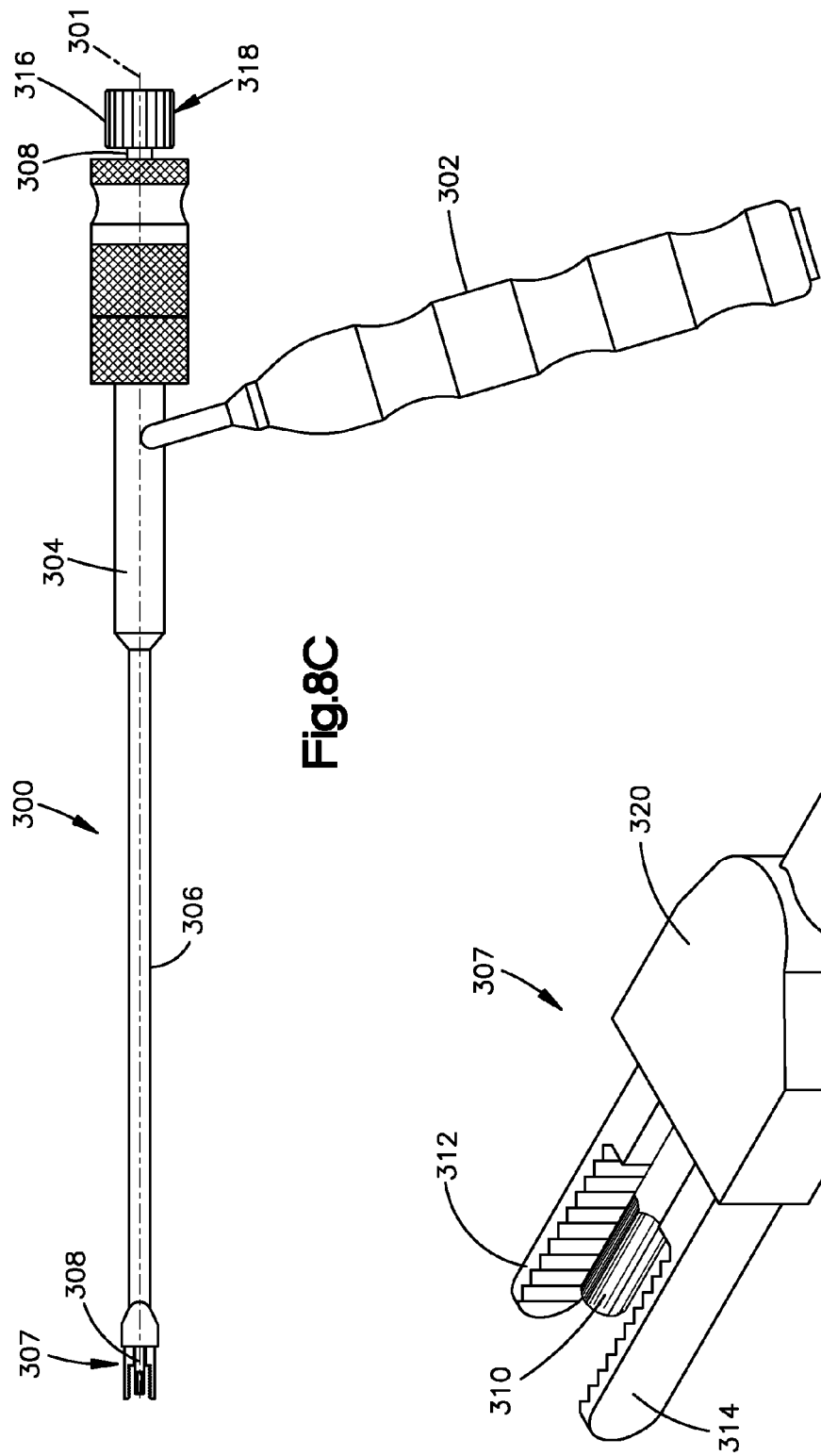

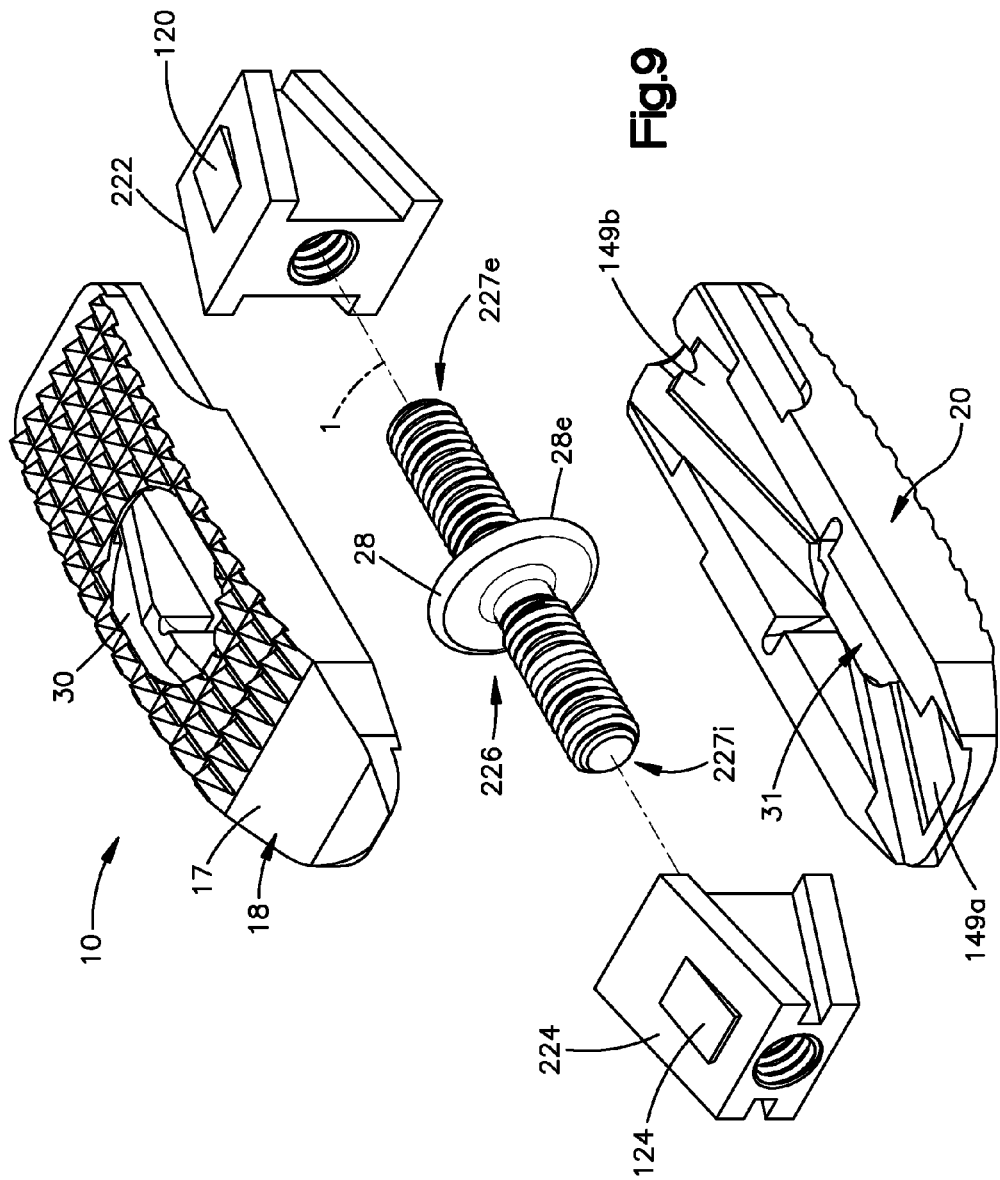

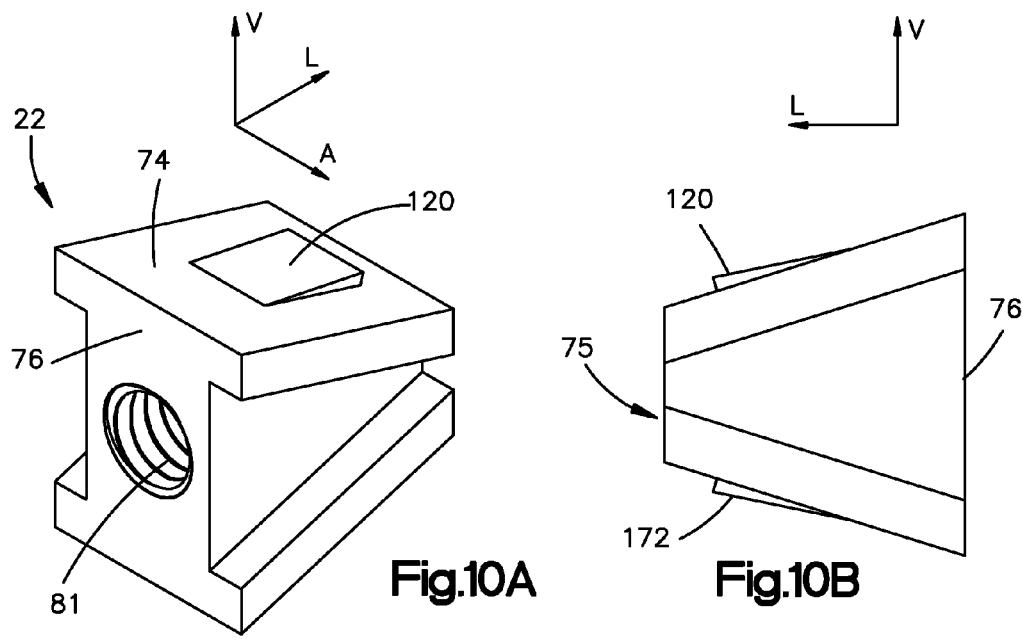
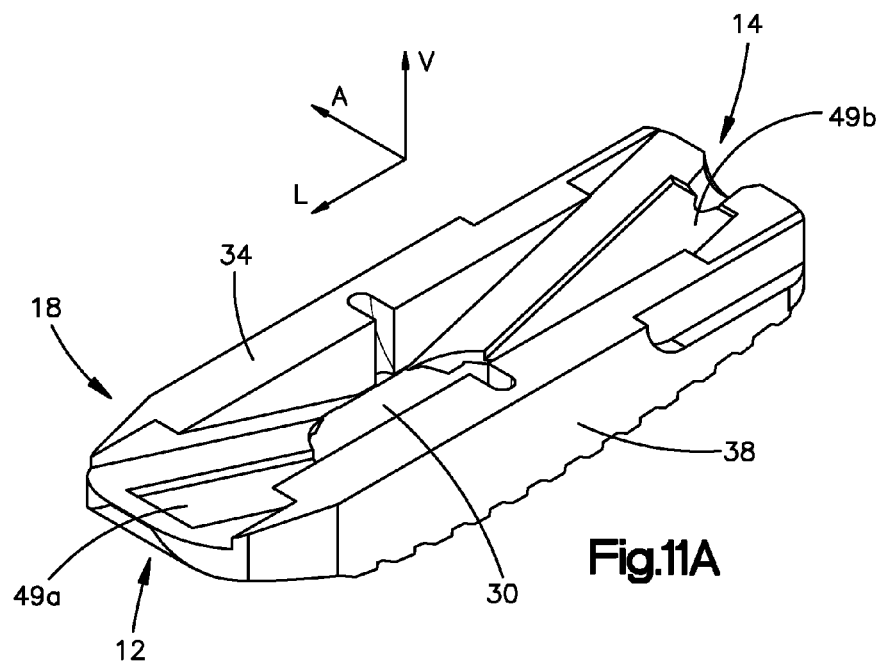

EXPANDABLE INTERVERTEBRAL IMPLANT, SYSTEM, KIT AND METHOD

TECHNICAL FIELD

The present invention relates to an expandable intervertebral implant, system, kit and method.

BACKGROUND

Removal of an intervertebral disc is often desired if the disc degenerates. Spinal fusion may be used to treat such a condition and involves replacing a degenerative disc with a device such as a cage or other spacer that restores the height of the disc space and allows bone growth through the device to fuse the adjacent vertebrae. Spinal fusion attempts to restore normal spinal alignment, stabilize the spinal segment for proper fusion, create an optimal fusion environment, and allows for early active mobilization by minimizing damage to spinal vasculature, dura, and neural elements. When spinal fusion meets these objectives, healing quickens and patient function, comfort and mobility improve. Spacer devices that are impacted into the disc space and allow growth of bone from adjacent vertebral bodies through the upper and lower surfaces of the implant are known in the art. Yet there continues to be a need for devices that minimize procedural invasiveness yet stabilize the spinal segment and create an optimum space for spinal fusion.

SUMMARY

According to an embodiment of the present disclosure, the expandable implant configured for insertion in an intervertebral space defined between a first vertebral body and a second vertebral body. The implant defines an insertion end spaced apart from a trailing end along a longitudinal direction. The implant can include a first plate and a second plate opposed to the first plate along a vertical direction that is perpendicular to the longitudinal direction. The implant can include a first wedge member and a second wedge member spaced from the first wedge member along the longitudinal direction, the first and second wedge members coupled to the first and second plates. Each wedge member defines a narrow end spaced apart from an inner end along the longitudinal direction, and the inner ends of each wedge member face other. The first and second wedge members configured to translate along the longitudinal direction along to the first and second plates from a first contracted configuration into a second separated configuration. The implant can include an actuation member coupled to the first wedge member and the second wedge member, the actuating member defining a flange extending toward the first and second plates, the actuation member configured to move the first and second wedge members from the first contracted configuration into the second separated configuration so as to separate the first and second plates from each other along the vertical direction.

BRIEF DESCRIPTION OF THE DRAWINGS

The foregoing summary, as well as the following detailed description of illustrative embodiments of the intervertebral implant of the present application, will be better understood when read in conjunction with the appended drawings. For the purposes of illustrating the expandable intervertebral implant of the present application, there is shown in the drawings illustrative embodiments. It should be understood, however, that the application is not limited to the precise arrangements and instrumentalities shown. In the drawings:

FIG. 4A is a perspective view of the interior surface of a plate of the implant shown in FIG. 1;

FIG. 4B is side view of a plate of the implant shown in FIG. 4A;

FIGS. 4C and 4D are bottom and top plan views, respectively, of a plate of the implant shown in FIG. 4A;

FIGS. 5A, 5B, 5C, and 5D are perspective, side, and opposing ends views of a wedge member used in the implant shown in FIG. 1;

FIGS. 6A and 6B are perspective and side views of the actuation member used in the implant shown in FIG. 1;

FIG. 8C is a side view of a tool according to another embodiment of the present disclosure;

FIG. 8D is a partial perspective view of an implant supporting end of a tool shown in FIG. 8C;

FIG. 9 is an exploded perspective view an implant according to another embodiment of the present disclosure;

FIGS. 10A and 10B are perspective and side views of a wedge member of the implant shown in FIG. 9;

FIGS. 11A and 11B are perspective and inferior plan views of a plate, respectively, of the implant shown in FIG. 9.

DETAILED DESCRIPTION OF ILLUSTRATIVE EMBODIMENTS

Figure 1:
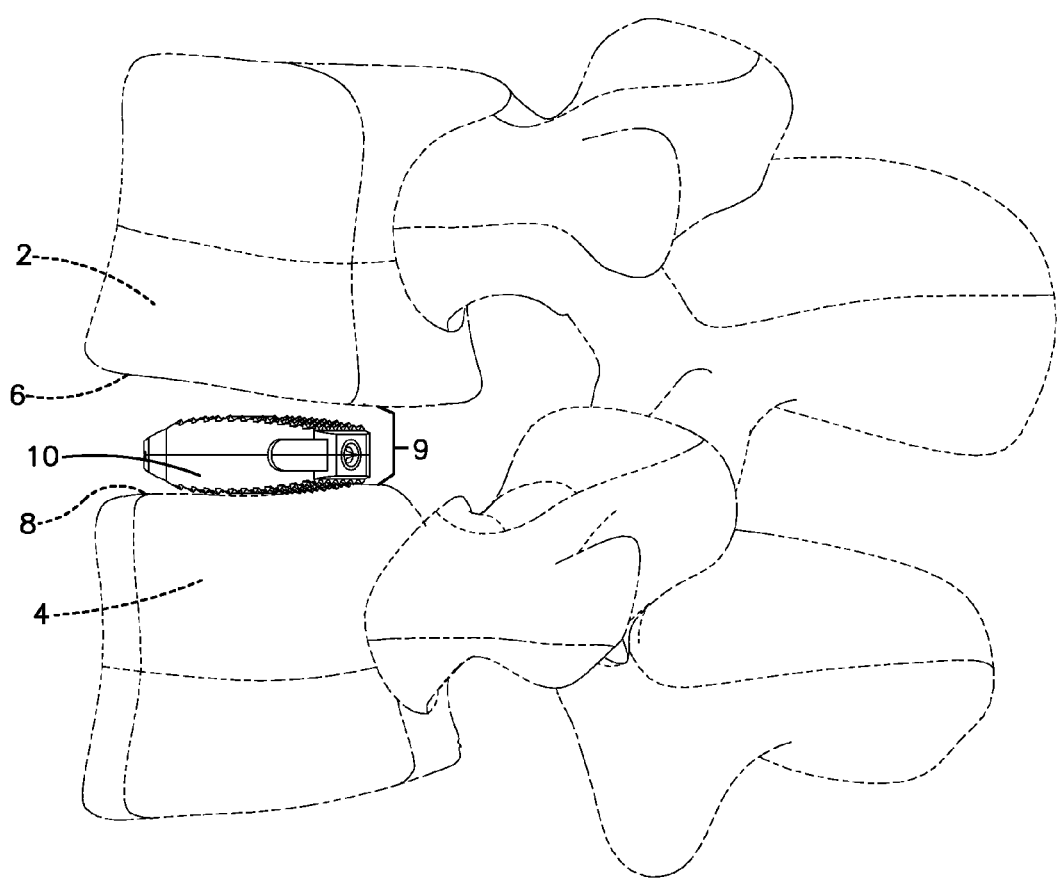
FIG. 1 illustrates an implant positioned between vertebral bodies, according to an embodiment of the present disclosure.
Figure 2A:
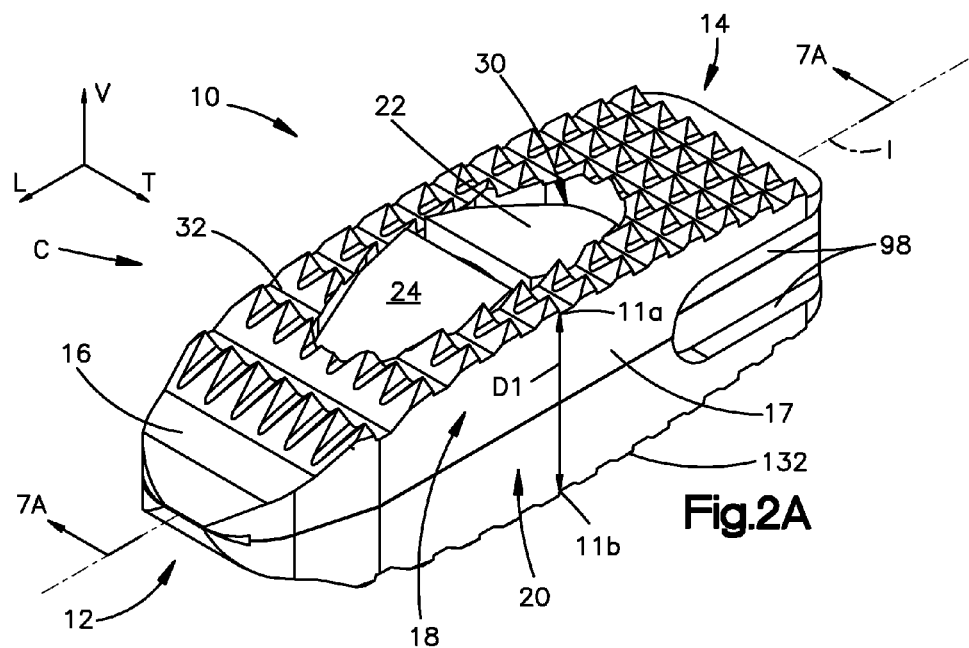
FIGS. 2A and 2B are perspective views of the implant shown in FIG. 1 in a collapsed configuration and an expanded configuration, respectively.
Figure 2B:
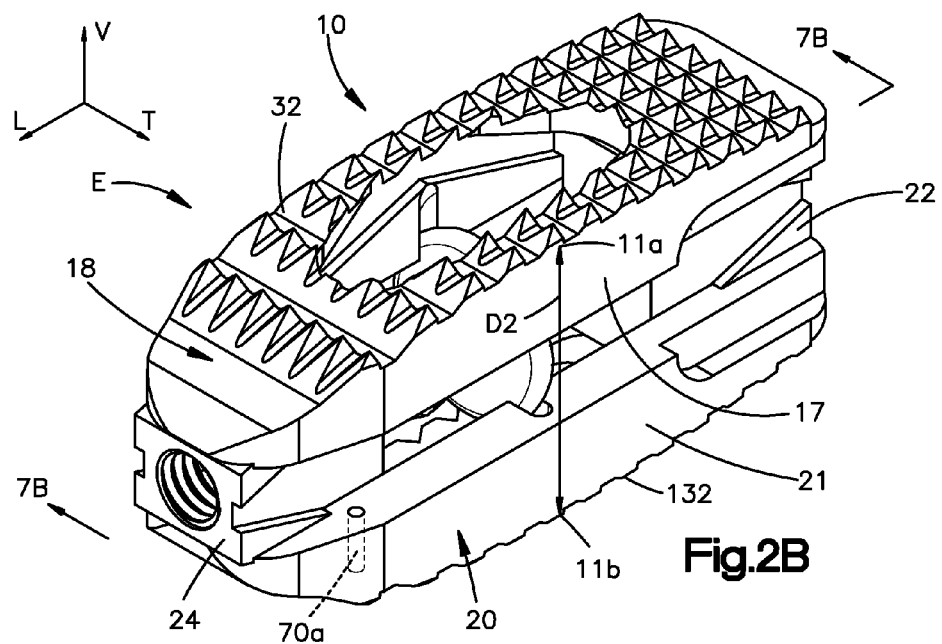

Referring to FIG. 1, a superior vertebral body 2 and an adjacent inferior vertebral body 4 defines an intervertebral space 9 extending between the vertebral bodies 2 and 4. The superior vertebral body 2 defines superior vertebral surface 6, and the adjacent inferior vertebral body 4 defines an inferior vertebral surface 8. The vertebral bodies 2 and 4 can be anatomically adjacent, or remaining vertebral bodies after a vertebral body has been removed from a location between the vertebral bodies 2 and 4. The intervertebral space 9 in FIG. 1 is illustrated after a discectomy, whereby the disc material has been removed or at least partially removed to prepare the intervertebral space 9 to receive an intervertebral implant or implant 10, as shown in FIGS. 2A-2B. The inserted and expanded implant 10 can achieve appropriate height restoration. The intervertebral space 9 can be disposed anywhere along the spine as desired, including at the lumbar, thoracic, and cervical regions of the spine.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

The implant 10 is described herein as extending horizontally along a longitudinal direction "L" and a transverse direction "T", and vertically along a vertical direction "V". Unless otherwise specified herein, the terms "longitudinal," "transverse," and "vertical" are used to describe the orthogonal directional components of various implant components and implant component axes. It should be appreciated that while the longitudinal and transverse directions are illustrated as extending along a horizontal plane, and that the vertical direction is illustrated as extending along a vertical plane, the planes that encompass the various directions may differ during use. For instance, when the implant 10 is inserted into an intervertebral space, such as the intervertebral space 9, the vertical direction V extends vertically generally along the superior-inferior (or caudal-cranial) direction, while the horizontal plane defined by the longitudinal direction L and transverse direction T lies generally in the anatomical plane defined by the anterior-posterior direction, and the medial-lateral direction. Accordingly, the directional terms "vertical" and "horizontal" may be used to describe the implant 10 and its components as illustrated merely for the purposes of clarity and illustration.

Figure 3:
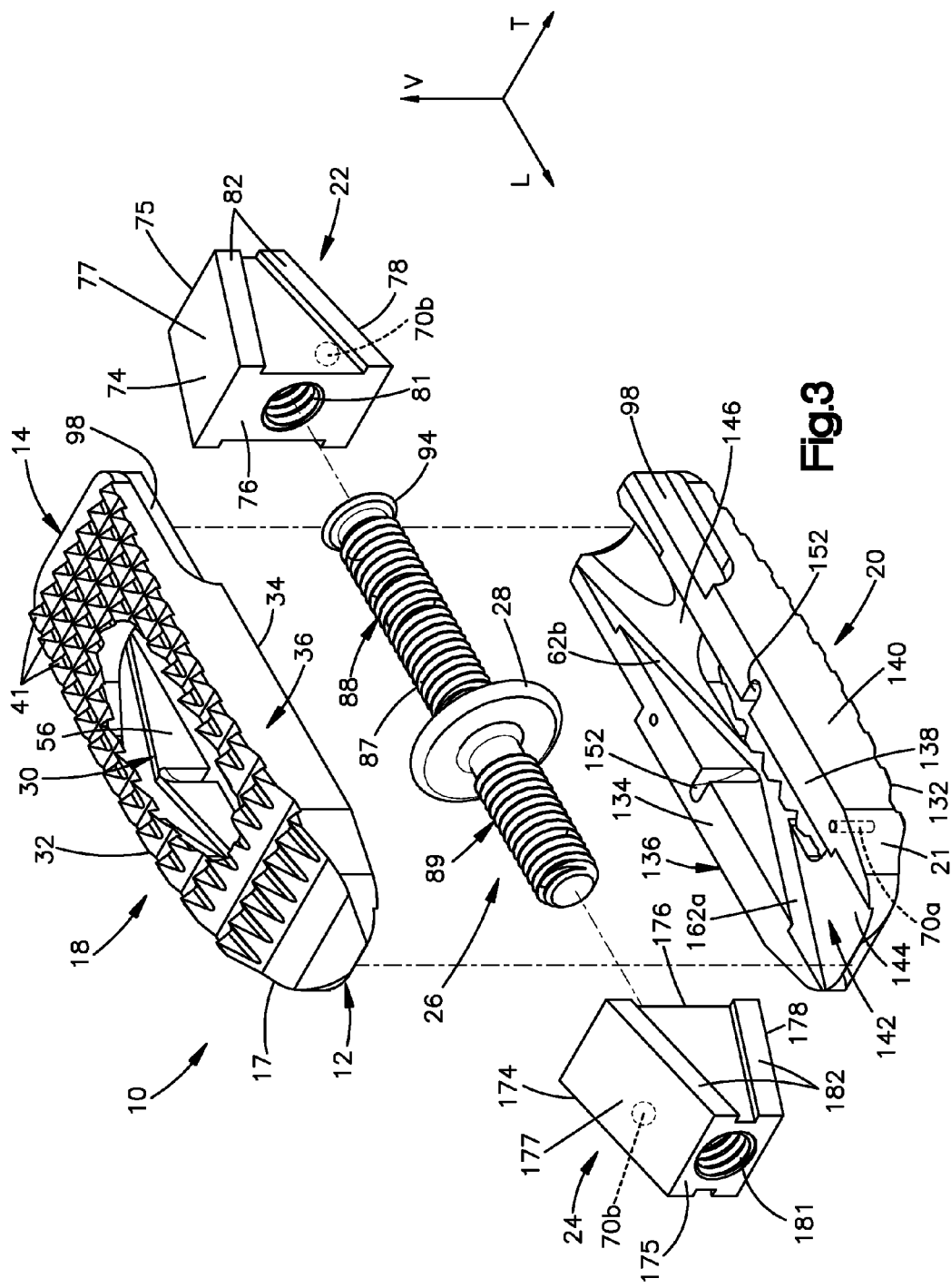
FIG. 3 is an exploded perspective view of the implant shown in FIG. 1.

Referring to FIGS. 1-3, the expandable intervertebral implant or implant 10 extends between a distal or insertion end 12 and proximal or trailing end 14 that is spaced from the insertion end 12 along an implant axis 1. The implant axis 1 can extend along the longitudinal direction L or any other linear or nonlinear direction as desired. The trailing end 14 is configured to couple with one or more insertion instruments, which are configured to support and carry the implant 10 into the intervertebral space 9, and/or actuate the implant 10 from a collapsed configuration C shown in FIG. 2A into an expanded configuration E shown in FIG. 2B. The implant 10 can also extend between an upper or first bone-contacting surface 32 and a lower or second bone contacting surface 132 spaced from the first bone-contacting surface along the vertical direction V. The bone contacting surfaces 32 and 132 are configured to engage opposing vertebral bodies 4 and 6, respectively. Each bone-contacting surface can be convex or partially convex, for instance, one portion of the surface is convex while another portion can be planar. The bone contacting surfaces 32 and 132 can also define a texture 41, such as spikes, ridges, cones, barbs, indentations, or knurls, which are configured to engage respective vertebral bodies 4 and 6 when the implant 10 is inserted into the intervertebral space 9. The bone contacting surfaces 32 and 132 may be partially textured. For instance, the bone contacting surfaces 32 and 132 can include specific patterns of textured and non-textured portions. As used herein, the term "proximal" and derivatives thereof refer to a direction from the distal or insertion end 12 toward the proximal end 14. As used herein, the term "distal" and derivatives thereof refer to a direction from the proximal end 14 toward the insertion end 12. As used herein, the term "superior" and derivatives thereof refer to a direction from the bone contact surface 132 toward the first bone-contacting surface 32. As used herein, the term "inferior" and derivatives thereof refer to a direction from the upper or first bone-contacting surface 32 toward the lower or second bone contacting surface 132.

Continuing with FIGS. 1-3, the implant 10 includes a first or superior plate 18, a second or inferior plate 20 opposing the superior plate 18 along the vertical direction V, and a pair of wedge members. The pair of wedge members include a first wedge member 22 and a second wedge member 24 that couple to the superior plate 18 to the inferior plate 20. The first and second wedge members 22 and 24 are translatable along the longitudinal direction or the implant axis 1 so as separate the superior plate 18 from the inferior plate 20 along the vertical direction V. The implant 10 can include an actuation member 26 coupled to the first wedge member 22 and the second wedge member 24. The actuation member 26 has a flange 28 protruding from the actuation member 26 along the vertical direction V toward the superior plate 18 and the inferior plate 20. The superior plate 18 can define a first lumen 30 and the inferior plate 20 can define a second lumen 31 aligned with and opposite to the first lumen 30. The implant 10 is configured such that when the implant 10 is in the collapsed configuration C shown in FIG. 2A, a portion of first wedge member 22 and the second wedge member 24 are disposed at least partially in the first lumen 30 and the second lumen 31. The implant plates and/or wedge members can be formed of polyether ether ketone (PEEK) or any other suitable biocompatible polymeric material. The actuation member can formed from a biocompatible polymeric material or metallic alloy, such as titanium or steel. It should appreciated that the any suitable material can be used to form the implant components as described herein.

Referring to FIGS. 3-4D, the superior plate 18 is configured for coupling with the first wedge member 22, the second wedge member 24, and at least a portion of the actuation member 26, for support on the flange 28. The superior plate body 17 can define a cavity 42 configured carry the first and second wedge members 22 and 24 are the actuation member 26. The superior plate 18 defines a first or superior plate body 17 that extends between the insertion end 12 and the trailing end 14 along the longitudinal direction L. The superior plate body 17 defines the first bone-contacting surface 32, and first and second interior plate contact surfaces 34 and 38 spaced from the bone-contacting surface 32 along the vertical direction V. The superior plate body 17 also defines first and second ramp surfaces 44 and 46 spaced from the bone contacting surface 32 along the vertical direction V. The plate body 17 further defines a first side 33a and a second side 33b opposite the first side 33a. The first and second sides 33a and 33b extend between the bone-contacting surface 32 and respective interior plate contact surfaces 34 and 38 along the vertical direction V. The plate body 17 also defines a first vertical surface 37 and a second vertical surface 39 that extend from the ramp surface 44 and 46 to respective interior plate contact surfaces 34 and 38 along the direction V. The plate body 17 thus defines a first sidewall 36 and a second sidewall 40 spaced from the first sidewall 36 along the transverse direction T. Specifically, the first sidewall 36 extends between the side 33a and vertical surface 37 along the transverse direction T, and from the ramp surfaces 44 and 46 to the interior plate contact surface 34 along the vertical direction V. The second sidewall 40 extends between the side 33b and vertical surface 39 along the transverse direction T, and from the ramp surfaces 44 and 46 toward the interior surface 38 along the vertical direction V. As illustrated, the cavity 42 extends along the longitudinal direction L of the plate body 17 and along the transverse direction T between opposing first and second walls 36 and 40. The first lumen 30 is in communication with the cavity 42 as detailed below. In the embodiment shown, the first and second walls 36 and 40 converge with the bone contacting surface 32 to form a tapered insertion end 16 (FIG. 2A).

Continuing with FIGS. 3-4D, the first and second walls 36 and 40 are configured to couple to the first and second wedge members 22 and 24. The first wall 36 can define at least one slot, for instance a first slot 52 for receiving a portion of the flange 28 of the actuation member 26. The first slot 52 is disposed in the first wall 36 at a location between the insertion end 12 and the trailing end 14 of the plate body 17. The second wall 40 can define at least one or second slot 54 for receiving another portion of the flange 28 of the actuation member 26. The second slot 54 is disposed in the first wall 36 at a location between the insertion end 12 and the trailing end 14 of the plate body 17. The second slot 54 is aligned, for instance transversely aligned, with and opposing the first slot 52 such that each slot 52 and 54 is positioned to receive a portion of the flange 28. The first and second slots 52 and 54 are also configured to mate with the structure of the flange 28. For instance, the first and second slots have an inner profile that is curvilinear and corresponds to the curvilinear profile of the flange 28. In other alternate embodiments, the first and second slots 52 and 54 may have a rectilinear shape. It should be appreciated that the slots 52 and 54 may have any desired shape that can slidingly receive a portion of the flange 28. For example, if the flange 28 has a square profile, the slots 52 and 54 can be configured to mate with the square shaped flange. In alternate embodiments, the first and second wall 36 and 40 can include a plurality of spaced slots spaced apart along the longitudinal direction L and disposed on the first and second walls 36 and 40 to receive a corresponding number of flanges or flanges portions protruding from the actuation member 26. For example, the first and second walls may include slots 52 and 54, and additional slots 52L and 54L (not shown) spaced apart from the slots 52 and 54 along the longitudinal direction (the longitudinal direction L).

The plate body 17, or for instance the first and second walls 36 and 40, can define one or more projections 56 and 58 that protrude from the walls 36 and 40 along the transverse direction T. The projections 56 and 58 are configured to engage a portion of the first and second wedge members 22 and 24 as further detailed below. In particular, the first wall 36 can define a first set of projections 56 that extend from the first wall 36 along the transverse direction T into the cavity 42. The first set of projections 56 can include a first wall projection 56a and a second wall projection 56b spaced proximally from the first wall projection 56a along the longitudinal direction L. In the illustrated embodiment, the first slot 52 separates the first wall projection 56a from the second wall projection 56a. The second wall 40 can define a second set of wall projections 58 that extend from the second wall 40 along the transverse direction T into the cavity 42. The second set of projections 58 can include a third wall projection 58a and a fourth wall projection 58b spaced proximally from the third projection 58a along the longitudinal direction L. In the illustrated embodiment, slot 54 separates the third wall projection 58a from the fourth wall projection 58b. While each wall 36 and 40 is illustrated has having two projections, each wall 36 and 40 can have a single projection, or more than two projections.

The plate body 17, for instance the first and second walls 36 and 40, can further define set of inclined connection grooves 60 and 62 configured to receive a portion of the first and second wedge members 22 and 24. The wall projections 56 and 58 protrude from respective walls 36 and 40 along the transverse direction T, as discussed above. The wall projections 56 and 58 are also spaced from the respective first and second ramp surfaces 44 and 46 along the vertical direction V to define the sets of inclined connection grooves 60 and 62. The first set of projections 56a and 56b extend from the first wall 36 so as to define first and second inclined connection grooves 60a and 60b respectively (FIG. 4A). The second connecting groove 60b is proximal disposed relative to the first connection groove 60a. The slot 52 is disposed between the first and second inclined connection grooves 60a and 60b. The second set of projections 58a and 58b extend from the first wall 40 to define third and fourth inclined connection grooves 62a and 62b, respectively. The fourth connection groove 62b is proximal to the third inclined connection groove 62a. The slot 54 is disposed between the inclined connection grooves 62a and 62b. The first and third projections 56a and 58a can also be referred to as the distally positioned projections, while the second and fourth projections 56b and 58b can be referred to as proximally positioned projections. Further, the first and third inclined connection grooves 60a and 62a can be referred to as the distally positioned connection grooves, while the second and fourth inclined connection grooves 60b and 62b can be referred to as the proximally positioned connection grooves.

Each opposing inclined connection grooves 60 and 62 extends from the lumen 30 toward the opposing implant or implant ends 12 and 14 along the longitudinal direction L. The plate body 17 can define a lumen first perimeter portion 68 and an opposing lumen second perimeter portion 69 that is spaced from the first perimeter portion 68 along the first lumen axis 85. Lumen perimeter portion 69 is disposed proximally toward the trailing end 14 of the implant 10 and lumen perimeter portion 68 is disposed distally toward the insertion end 12 of the implant 10. The distally positioned grooves 60a and 62a extend distally from the first perimeter portion 68 of the lumen 30 toward the plate insertion end 12, while the proximally positioned grooves 60b and 62b extend proximally from the second perimeter portion 69 of the lumen 30 toward the trailing end 14. The inclined connection grooves 60 and 62 can thus slidably receive therein the ridges 82 and 182 of the first and second wedge members 22 and 24.

Figure 7A:
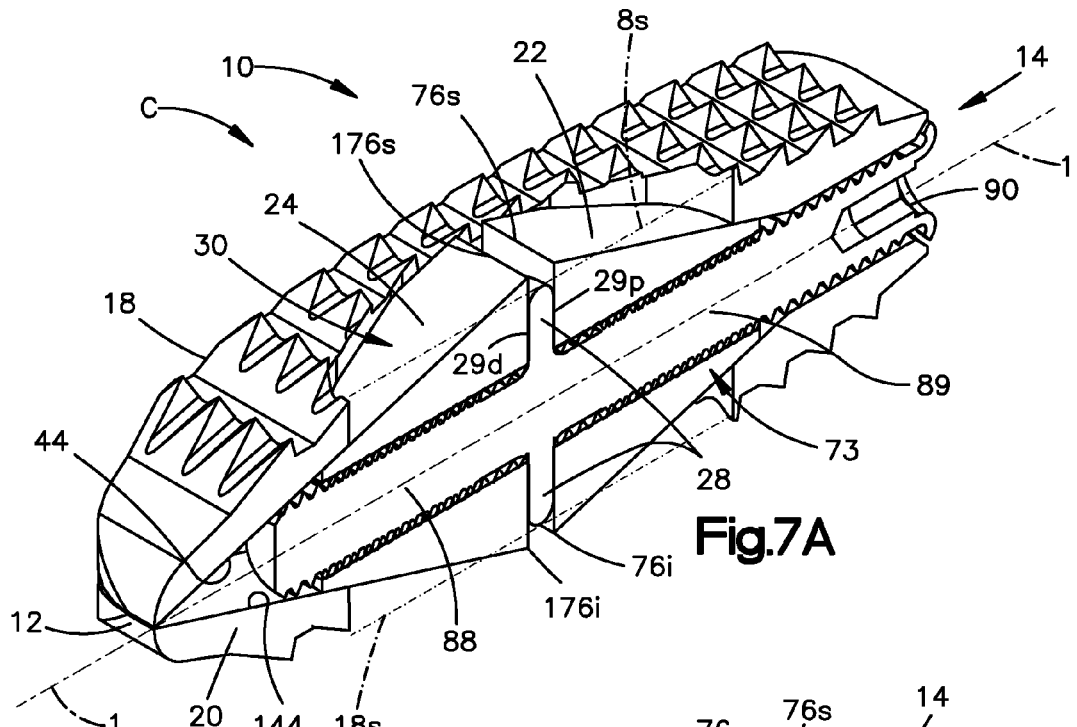
FIGS. 7A and 7B are sectional views of the implant taken along lines 7-7 in FIGS. 2A and 2B, illustrating the collapsed and expanded configurations.

Continuing with FIGS. 3-4C, the plate body 17 defines ramp surfaces 44 and 46, for instance a first ramp surface 44 and a second ramp surface 46 that are configured to mate with and slide along portions of the first and second wedge members 22 and 24. The first ramp surface 44 extends from the first perimeter portion 68 of the lumen 30 distally generally along the longitudinal direction L to the insertion end 12. The ramp surface 44 is inclined to abut and slidingly receive a portion of the second wedge member 24. The second ramp surface 46 extends from the second perimeter portion 69 of the lumen 30 proximally along the longitudinal direction L toward the trailing end 14. The ramps surfaces 44 and 46 also extend transversely along the transverse direction T between the opposing first and second plate walls 36 and 40. Each ramp surface 44 and 46 can define a ramp angle β (not shown) defined with respect to interior plate contact surfaces 34 and 38. It should be appreciated that the angle β can vary as needed. The plate body 17 can also define a curvilinear portion 48 disposed at the trailing end 14 of the plate body 17 and in communication with the second ramp surface 46. The curvilinear portion 48 is configured align with a corresponding curvilinear portion 148 on the inferior plate 20. When the plates 18 and 20 are in the collapsed configuration as shown in FIGS. 2A and 7A, the curvilinear portions 48 and 148 define an access opening 50. The access opening 50 that provides access the actuation member 26, as further detailed below.

Continuing with FIGS. 3-4D, the superior plate 18 can include one or more radiographic markers. The plate body 17 can define one or more bores (not shown) sized and dimensioned to receive a radiographic marker 70a therein. As illustrated, the radiographic marker 70a is disposed in the second wall 40 and positioned toward insertion end 12 of the plate 18. The opposing plate 20 can have a radiographic marker 170a as well. When the implant 10 is inserted into the intervertebral space 9, and the implant 10 is expanded from the first configuration C to the expanded configuration E, the markers 70a and 170a can separate along the vertical direction V. With image analysis, the extent of plate separation can be determined or indicated by observing the extent of separation between the markers 70a and 170a disposed in the superior plate 18 compared to marker disposed in the inferior plate 20.

The inferior plate 20 is configured similarly to the superior plate 18. The inferior plate 20 thus includes similar structural features that correspond to the structural features described above with respect to the superior plate 18. The inferior or second plate 20 defines a plate body 21 that extends between the insertion end 12 and the trailing end 14 along the longitudinal direction L. The inferior plate body 21 defines a second bone contacting surface 132, first and second plate contact surfaces 134 and 138 spaced from the bone contacting surfaces 32 along the vertical direction V, and first and second ramp surfaces 144 and 146 spaced from the bone contacting surfaces 32 along the vertical direction V. The inferior plate body 21 therefore defines define cavity 142, first and second walls 136 and 140, a first set of projections 156a-b, a second set of projections 158a-b, and inclined connection grooves 160a-b, 162a-b. The interior surfaces 134 and 138 of the inferior plate 20 are configured to oppose and contact the interior contact surfaces 34 and 38 of the superior plate 18. The superior plate 18 and inferior plate 20 can define opposing indentations 98 and 99 at the trailing end 14 of the implant 10. The indentations 98 and 99 are configured to receive a portion of an insertion tool 100 and 300 (FIG. 8A-8F).

The first and second plates 18 and 20 can also define the respective first and second lumens 30 and 31 as discussed above. Each lumen 30 and 31 has been configured to configured receive at least a portion of the first and second wedge members 22 and 24 to maximize the compact design and the expansion characteristics of the implant 10. The lumens 30 and 31 partially receiving portions of the first and second wedge members 22 and 24 when the implant 10 is in the collapsed configuration C (FIG. 2A), which allows for the dimensions of the first and second wedge members 22 and 24 to be increased over wedge members used in implants with lumens not configured to permit a portion of the wedge member to extend therethrough. Further, the configured first and second wedge members 22 and 24 can improve implant 10 stability when expanded. Thus, the implant 10 has a collapsed configuration that is compact and less invasive, and an expanded configuration that is dimensionally stable. The lumens 30 and 31 have the additional benefit of promoting bone growth when implanted in the intervertebral space 9. The first lumen 30 and second 31 are generally elongate in the longitudinal direction L. The lumens 30 and 31 can have other shapes, for instance the lumens can be circular (FIGS. 9-11B). The lumen 30 extends through the superior plate body 17 along the vertical direction V into communication with the cavity 42. Likewise, the second lumen extends through the second or inferior plate body 21 into communication with the cavity 142. The superior plate body 17 can define a lumen axis 85 that extends along the longitudinal direction L of plate body 17. The lumen axis 85 is aligned with the bone-contacting surface 32 or at leady portion thereof, for instance the lumen axis 85 is spaced from the implant axis 1 along the vertical direction V with a portion of the bone-contacting surface 32. The plate body 17 can also define a lumen first perimeter portion 68 and an opposing lumen second perimeter portion 69 that is spaced from the first perimeter portion 68 along the first lumen axis 85. Lumen perimeter portion 68 is disposed proximally toward the implant trailing end 14 and lumen perimeter portion 69 is disposed distally toward the implant insertion end 12. Likewise, the inferior plate body 21 can define a second lumen axis 85a (not shown) that extends along the longitudinal direction L of plate body 21 and is aligned along the vertical direction V with bone contacting surface 132. The plate body 21 can also define a lumen first perimeter portion 168 and an opposing lumen second perimeter portion 169 that is spaced from the first perimeter portion 168 along the second lumen axis 85a. Lumen perimeter portion 168 is disposed proximally toward the trailing end 14 and lumen perimeter portion 169 is disposed distally toward the implant insertion end 12.

Referring to FIGS. 3, 5A-5D, the first wedge member 22 and the second wedge member 24 are configured for slidable coupling to the superior and inferior plates 18 and 20. The first and second wedge members 22 and 24 are configured similarly, and for illustrative purposes, only the first wedge member 22 will be described below. The first wedge member 22 defines a wedge body 74 extending along a wedge axis 3 between a narrow end 75 and an inner end 76 spaced from the narrow end 75. The wedge axis 3 is generally aligned with the implant axis 1 and extends along the longitudinal direction L. As show in FIGS. 3 and 7A, the first wedge narrow end 75 is positioned toward the outer or trailing end 14 of the implant 10, while the inner end 76 is positioned to face the distal or insertion end 12 of the implant 10. Further, the second wedge member 24 has a wedge body 174 that extends from a narrow end 175 to an inner end 176 along the wedge axis 3, wherein the narrow end 175 is positioned toward the distal or insertion end 12 of the implant 10 and the inner end 176 is positioned toward the proximal or trailing end 14 of the implant. Thus, the first wedge member 22 is positioned such that the inner end 76 of the first wedge member 22 and faces the inner end 176 of the second wedge member 24.

The body 74 defines a superior tip 76s spaced from an inferior tip 76i along a vertical direction V and disposed at the inner end 76. A first or inner wedge dimension H1 is defined as the distance between the superior and inferior tips 76s and 76i along the vertical direction V. The plate body 17 can define first plate dimension L51 extending between the bone contacting surface 32 and the interior contact surfaces 34 and 38, while the plate body 21 can define a second plate dimension 52 extending between the bone contacting surface 132 and the inner surfaces 134 and 138. In an embodiment, the first or inner wedge dimension H1 is about twice the distance of the first plate dimension S. In an embodiment, the first or inner wedge dimension H1 can be greater than or equal to the sum of the first plate dimension S and the second plate dimension 52. In an embodiment, the first or inner wedge dimension H1 can be less than or equal to sum of the first plate dimension S1 and second plate dimension 52.

The body 74 defines a wedge shape configured for slidable coupling to the first and second plates 18 and 20. The body 74 defines a first or superior inclined surface 77 and a second inclined or inferior inclined surface 78 opposite the first incline surface 77. The first and second inclined surfaces 77 and 78 extend along the longitudinal direction L from the inner end 76 toward the narrow end 75. The first inclined surface 77 is angularly offset from a second inclined surface 78. In an embodiment, the first and second inclined surfaces form an angle θ defined between intersecting lines coincident with the first and second inclined surfaces 77 and 78 (FIG. 5B). Angle θ can vary as needed. The first inclined surface 77 can slidably mate with a ramp surface 46 on an interior the superior plate 18, while the second inclined surface 78 can slidably mate with a first ramp surface 146 on of the inferior plate 20. The body further defines a first side 79 and a second side 80 opposite the first side 79. The first and second sides 79 and 80 extend along the longitudinal direction L between the inner end 76 and the narrow end 75, and vertically along the vertical direction V between the first and second inclined surfaces 77 and 78.

The first wedge member 22 also includes one or more ridges 82 (82a-d) protruding from the body 74 along the transverse direction T. The ridges 82 are configured to couple the first wedge member 22 to the superior plate 18 and inferior plate 20. For instance, the one or more ridges 82 are slidably coupled to respective portions of the inclined connections grooves 60, 62 160, 162. Each ridge 82a-82d extends between the narrow end 75 and the inner end 76 of the body 74 generally along the wedge axis 3. Ridges 82a-82d also extend along the respective first and second inclined surfaces 77 and 78. Ridges 82a and 82c are angled only offset action angle with respect to ridges 82b and 82d. The vertically spaced apart ridges 82c and 82d disposed on the first side 79 of the body 74 can define a recess portion 86 which can receive the distally oriented projections 56b and 156b of the plates 18 and 20, respectively. The vertically spaced apart ridges 82a and 82b are disposed on the side 80 define recess portion 84 which receives the distally oriented projections 58b and 158b of the plate 18 and 20. The transversely spaced apart ridges 82a and 82c are received in the inclined connection grooves 60b and 62b of the superior plate. The other transversely spaced apart ridges 82b and 82d are received in the inclined connection grooves 160b and 162b of the inferior plate 20 (FIG. 3).

The wedge member body 74 also defines first bore 81 extending through the body 74 between the narrow end 75 and the inner end 76 along the wedge axis 3. The first bore 81 is configured to receive at least a portion of the actuation member 26. In an embodiment, the bore 81 is internally threaded to mate with a corresponding threaded portion of the actuation member 26. Further, the wedge member body 74 includes an additional bore or receiving a radiographic marker 70b therein.

The second wedge member 24 is configured similarly to the first wedge member 22. The second wedge member 24 defines a second body 174. The body 174 defines a narrow end 175 spaced apart from an inner end 176 along the wedge axis 3, first and second inclined surfaces 177 and 178, a plurality of ridges 182 extending from body 174, and a second bore 181 extending through the body 174 between the narrow and inner ends 175 and 176. The first and second sides 179 and 180 extend between the inclined surfaces 177 and 178. The body 174, for instance the body inner end 176 defines a superior tip 176, spaced apart from an inferior tip 176i along a vertical direction V. The second wedge member has a wedge dimension H2 (not shown) defined as the distance between the superior tip 176s and the inferior tip 176i. H2 can be equal to H1. As shown in FIG. 3, the second wedge member 24 is spaced apart from the first wedge member 22 along the longitudinal direction L such that the inner end 175 of the second wedge member 24 faces the inner end 75 of the first wedge member 22. The second wedge member 24 also includes ridges 182a-182d that are similar to ridges 82a and 82d.

Continuing with FIGS. 3-4D, the actuation member 26 is configured to couple the first and second wedge members 22 and 24 together while also providing stability to the superior plate 18 and inferior plate 20 during implant expansion. The actuation member 26 extends along the longitudinal direction L between a distal end 27i and a proximal end 27e. The actuation member 26 defines a shaft 87 extending between the opposed ends 27i and 27e. The flange 28 protrudes from the shaft 87 along the transverse T or a radial direction R. The flange 28 defines a flange body 28b, a distal facing surface 29d and a proximal facing surface 29p spaced from the distal facing surface 29d along the longitudinal direction L. The flange body 28b is sized and dimensioned to slide within the slots 52 and 54 of plate 18, and slots 152 and 154 of the plate 20. The radial direction R can be aligned with the transverse direction T and the vertical direction and is used to indicate that the flange 28 protrudes radially from the shaft 87. The flange 28 can have other configurations, and as such Cartesian coordinates may better indicate directional components.

The shaft 87 can define a first threaded portion 88 disposed proximally relative to the flange 28, and a second threaded portion 89 disposed distally from the flange 28. The first shaft portion 88 can have a length L1 extending from the flange proximal face 29p to the proximal end 27e, and the second threaded portion 89 has a second length L2 extending from the flange distal face 29d to the distal end 27i, wherein the first length L1 is greater than the second length L2. The shaft 87 is configured to extend through the bore 81 of the first wedge member 22 and into the curvilinear portions 48 and 148 or access opening 50 of the plates. The first threaded portion 88 has a thread pattern that is oriented in the opposite direction of the thread pattern formed on the second threaded portion 89. The internal threads of the first and second bores 81 and 181 are in opposing orientations such that when the actuation member 26 rotates, the first and second wedge members 22 and 24 translate along the actuation member 26 toward each other or away from each depending on the rotation direction of the actuation member 26. The thread pattern on each portion may have the same pitch such that the first and second wedge members 22 and 24 can translate along the actuation member 26 at the same rate. The thread pitch can be different if needed when different distraction profiles are desired in the expanded configuration (e.g. kyphotic or lordotic). The proximal end 27e of the actuation member 26 can define a lip 94 configured to abut the narrow end 75 of the first wedge member 22. The lip 94 and can help prevent displacement of the actuation member 26 from the first wedge member 22. The proximal end 27e of the actuation member 26 can define a socket 90 configured to receive or support a portion of an instrument, as further detailed below. The socket 90 can have any configuration ass need to receive an instrument, such as hex, Phillips, flat, star, etc.

The implant 10 as described herein can have initial dimensions and expanded dimensions. For, instance, the implant can have first implant height D1 defined between opposing portions 11a and 11b of the first and second bone contacting surfaces 32 and 132, and second implant height D2 defined between opposing portions 11a and 11b of the first and second bone contacting surfaces 32 and 132 when the implant is expanded (FIGS. 2A and 2B). In an embodiment, the first implant height D1 can range between 7 mm and 10 mm, and the second expanded height can range between 10 mm and 13 mm. For instance, in an embodiment, the first height can be 7 mm while the expanded, second height can be 10 mm. In another embodiment, the first height can be 9 mm and the expanded, second height D2 can be 13 mm. Other dimensions are possible as well. For example first heights can be up to 7 mm, 9 mm, or greater. The implant 10 can have length E defined between the distal or insertion end 12 and the proximal or trailing end 14. The length E can range between 24 mm and 32 mm. The length E, however, can be shorter than 24 mm or greater than 32 mm. Further, the implant is configured such the length E of the implant 10 is consistent regardless of when the implant 10 is in the collapsed configuration or when the implant 10 is in the expanded configuration. That is, the first and second wedge members 22 and 24 are configured such the opposed narrow ends 75 and 175 translate to, but do not protrude from the implant trailing end 14 or implant insertion end 12 when in the expanded configuration. This configuration improves implant stability.

Figure 8A:
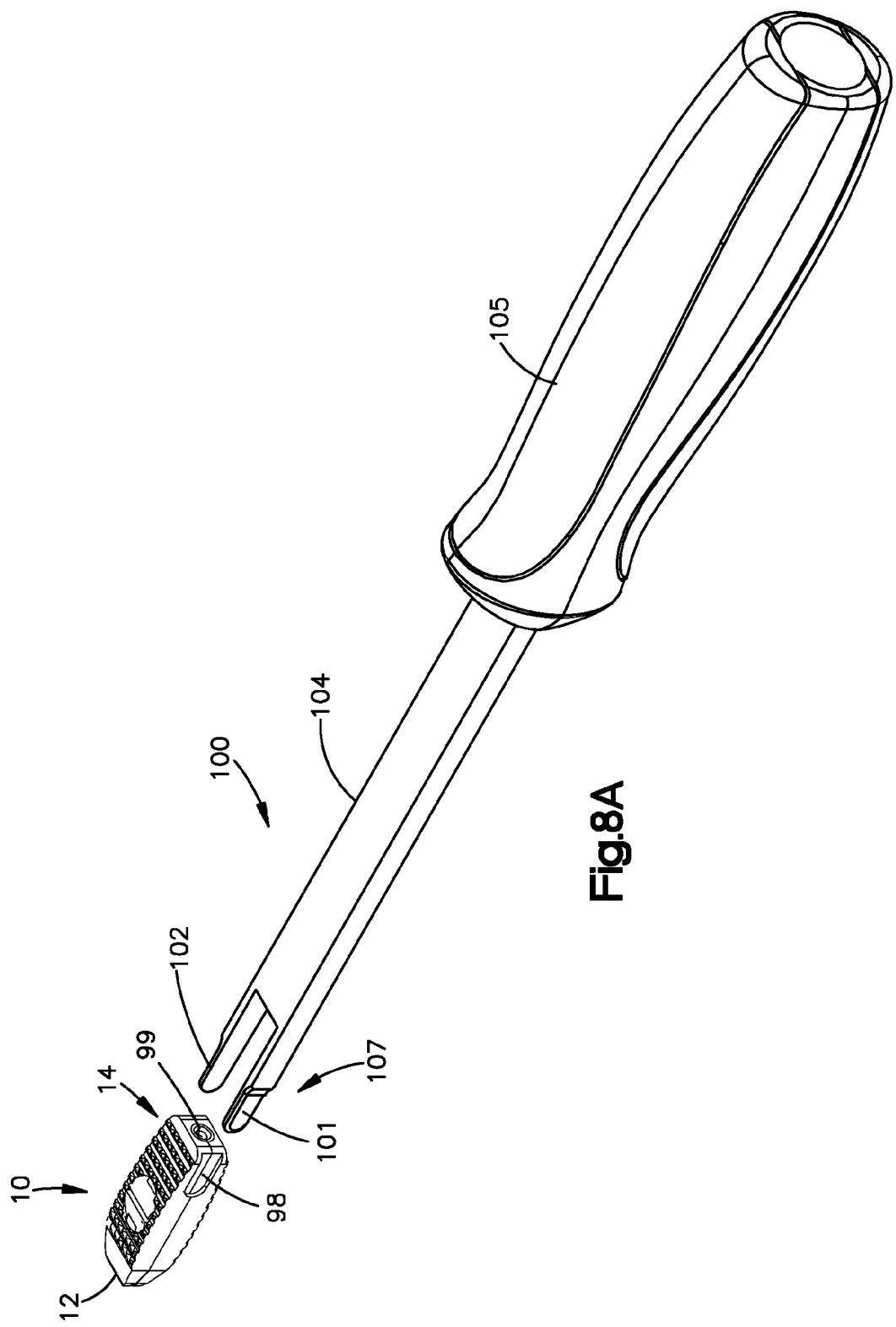
FIG. 8A is a perspective view of an insertion tool used to insert the implant shown in FIG. 1 into an intervertebral space.
Figure 8B:
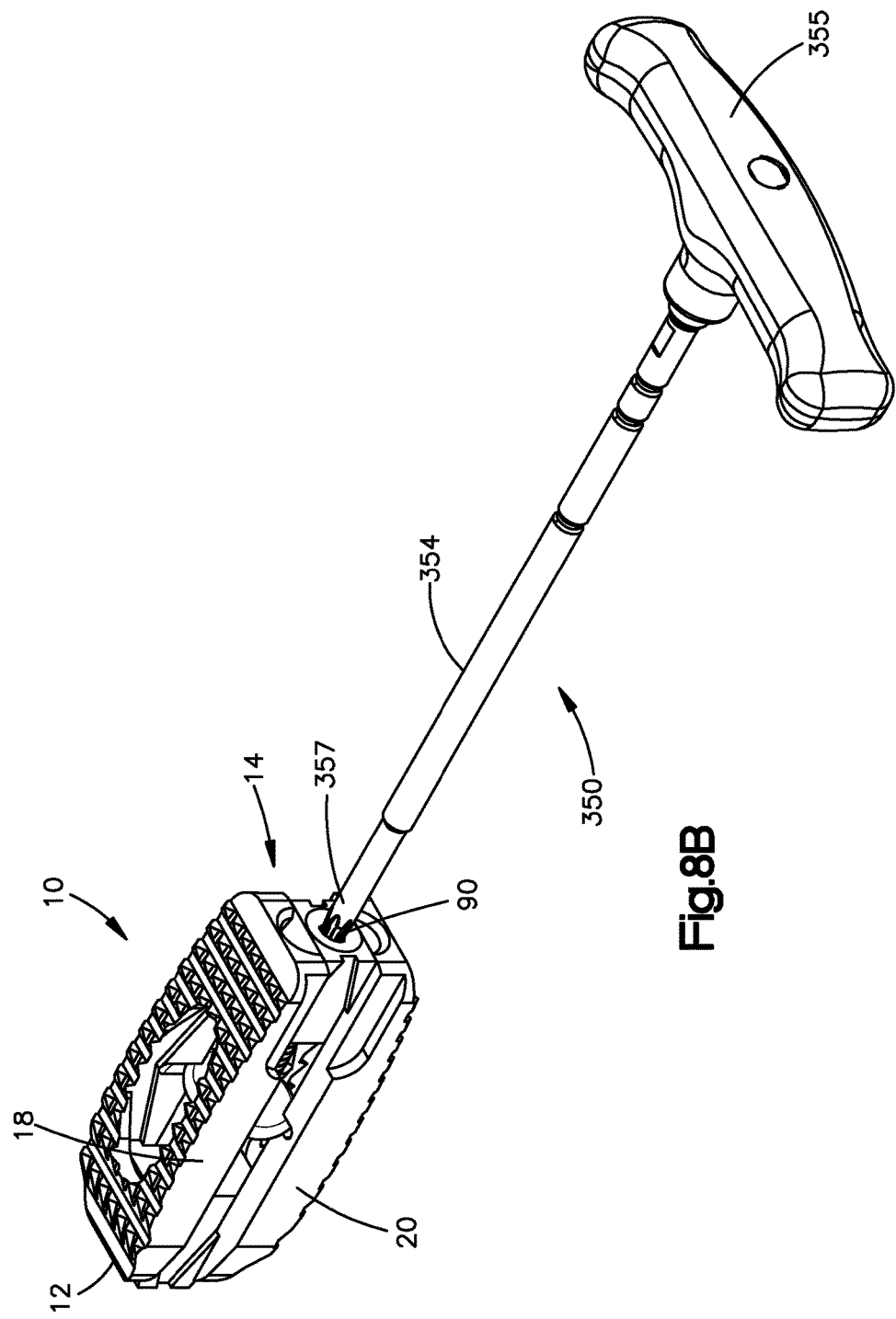
FIG. 8B is a perspective view of a tool engaged with the trailing end of the implant shown in FIG. 1.

Referring to FIGS. 8A-8C, the system as described herein includes one or more insertions tools. An insertion tool 100 can include a handle 105 and a shaft 104 extending from the handle toward an implant supporting end 107. The implant supporting end 107 is configured to support, for instance carry or engage with a portion of the implant 10. The implant supporting end 107 can include spaced apart tabs 101 and 102 configured and sized to be received in the implant indentations 98 and 99. When the implant tabs 101 and 102 engage the indentations 98 and 99, the tool 100 can position and/or insert the implant 10 into the intervertebral space 9. An additional tool 350 can be used to expand the implant 10 from the collapsed configuration to the expanded configuration. The tool 350 can include a handle 355 and a shaft 354 extending from the handle toward an implant supporting end 357. The implant supporting end 357 is configured to engage the actuation member 26, such that rotation of the tool 350 can cause rotation of the actuation member 56.

Figure 8E:
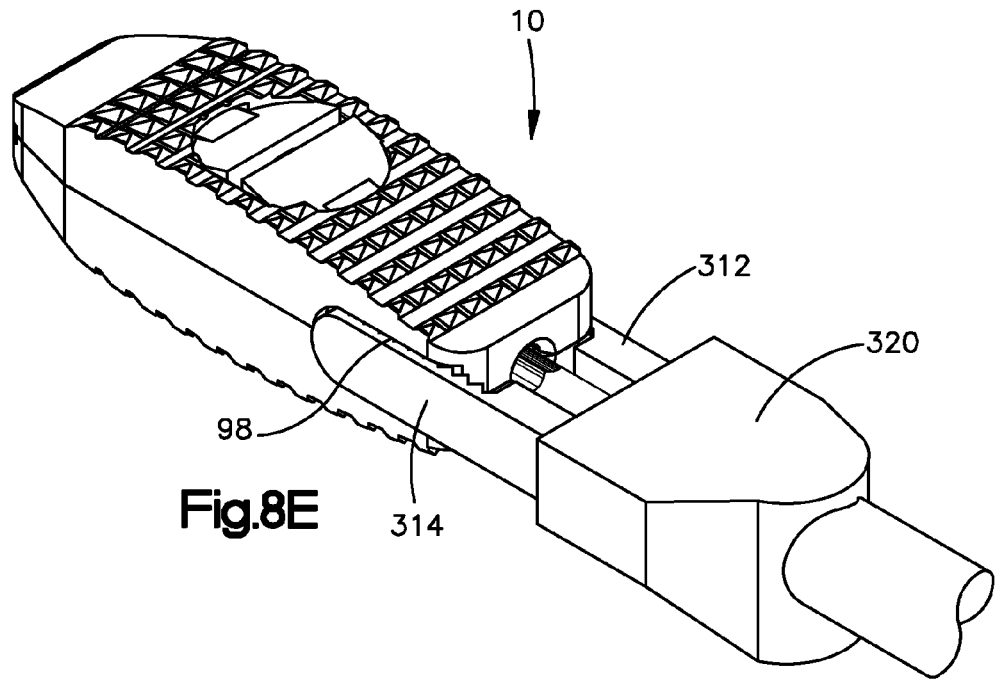
FIGS. 8E and 8F are partial perspective views of the tool shown in FIG. 8D supporting an implant.
Figure 8F:
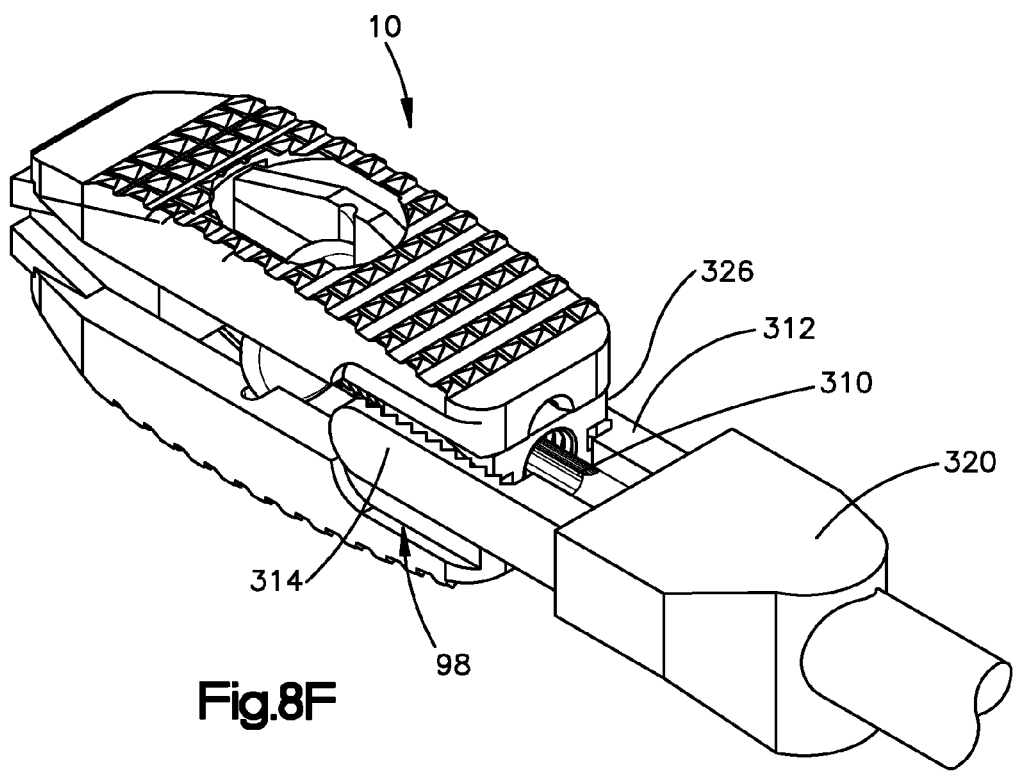
Figure 11B:
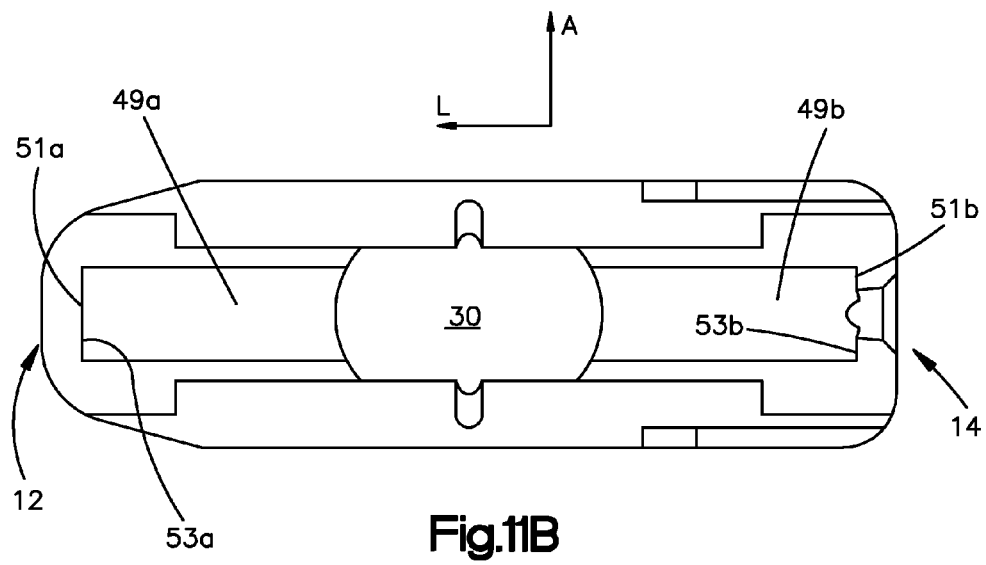
Figure 12:
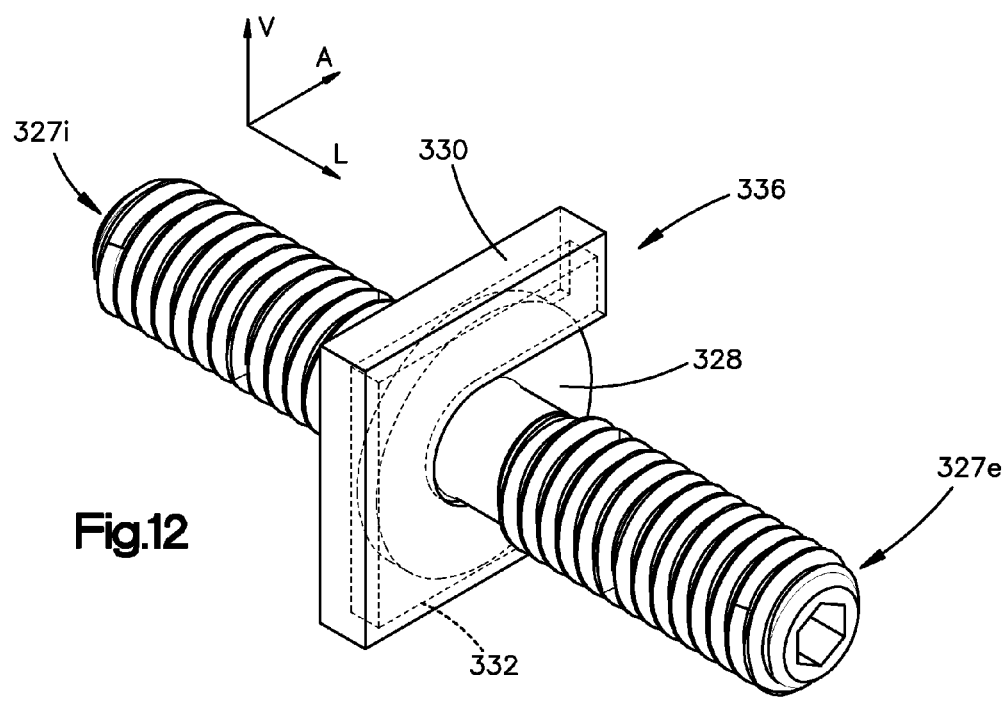
FIG. 12 is a perspective view of an actuation member in accordance with another embodiment of the present disclosure.

Referring to FIGS. 8D-8E, another embodiment a tool 300 can include a handle 302, tool housing 304 connected to the handle 302, and an elongate cannulated shaft 306 extending from the housing 304 toward an implant supporting end 307. The housing 304 and cannulated shaft 306 are elongate along an insertion tool axis 301. The housing 304 and cannulated shaft 306 define a cannulation (not shown) that extends through the housing 304 and shaft 306. The tool 300 also includes rotation member 318 that defines a rotation member 316 and an elongate rod 308 that extends from the rotation member 318 toward an engagement end 310 along the axis 301 as shown in FIG. 8D. The rotation member 318 is rotatable in the cannulation as well as slidable or translatable in the cannulation along the tool axis 301. The tool implant supporting end 307 includes a body 320 and tabs 312 and 314 extending from the body. The engagement end 310 of the rod 308 protrudes from the body 320 and is disposed between the tabs 312 and 314. Tool 300 can be used to clasp, insert, and then expand the implant. The tool 300 can be used clasp the implant 10 by inserting the tabs 312 and 314 into the indentations 98 and 99 while the rotation member 318 can be slide into engagement with the actuation member 26. For instance, the engagement end 310 can be coupled to the opening 90 in the actuation member 26 while tabs 312 and 314 support the implant 10. The rotation member 318 can be rotated relative to the shaft 306 so that the actuation member 26 is rotated.

Figure 7B:
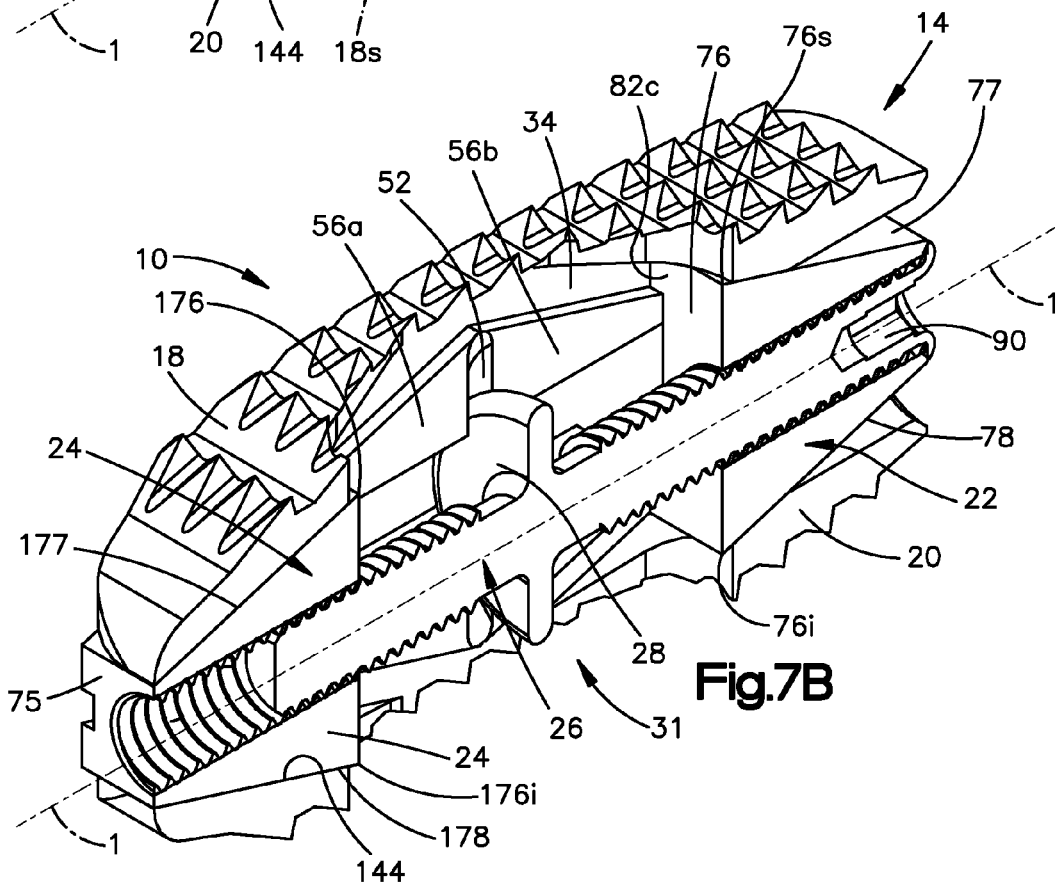

Referring to FIGS. 7A and 7B, implant 10 is configured to expand from the collapsed configuration C (FIG. 7A) to the expanded configuration E (FIG. 7B). When the first or collapsed configuration C, the first and second wedge members 22 and 24 are disposed in the implant such that the inner ends 76 and 176 face and are spaced apart from each other to define a gap therebetween. The actuation member 26 is coupled to the first and second wedge members 22 and 24 such that the first threaded portion 88 is disposed in the first bore 81 and the second threaded portion 89 is disposed in the second bore 181. The flange 28 extends between (in the sup) and along the opposed inner ends 76 and 176 of the first and second wedge members 22 and 24. The inclined surfaces 77 and 78 are adjacent to opposing plate ramp surfaces 46 and 146, while the second wedge member 24 inclined surfaces 177 and 178 are adjacent to opposing plate ramp surfaces 44 and 144. The inner end superior tips 76s and 176s extend into the lumen 30 and an into a plane containing the bone contacting surface 32, while the inner end tips 76i and 176i extend into the second lumen and to a plane containing the bone contacting surface 132. The flange distal face 29d abuts the inner end 176 of the second wedge member 24, while the flange proximal face 29p abuts the inner end 76 of the first wedge member 22. Portions of the first and second wedge members 22 and 24, for instance tips 76s-i and 176s-i, disposed in the lumens 30 and 31 allows for a wedge profile that aids plates 18 and 20 separation with relatively little advancement of the first and second wedge members 22 and 24 along the actuation member 26. For instance, the superior tips 76s and 176s extend to, for instance traverse, the first lumen axis 85 such that the tips are generally aligned with the bone contact surface 32 of the superior plate 18. The inferior tips 76i and 176i extend to, for instance traverse, the second lumen axis 85a such that the tips 76i and 176i are generally aligned with the bone contact surface 132 of the inferior plate 20.

Turning to FIGS. 7B and 8A-8F, when the actuation member 26 is rotated for via a tool 150 or 350, the first threaded portion 88 of the actuation member 26 causes the first wedge member 22 to translate toward the trailing end 14 of the implant 10. The inclined surfaces 77 and 78 bears against the ramp surfaces 46 and 146 to separate the superior plate 18 from the inferior plate 20 along the vertical direction. The ridges 82a-d slide along inclined connection grooves 60b, 160b, 62b, 162b (not shown in the FIG. 7B). While the first wedge member 22 is translating toward the implant trailing end 14, the second threaded portion 89 of the actuation member 26 engages the second bore 181 and causes the second wedge member 24 to translate toward the insertion end 12 of the implant 10. The inclined surfaces 177 and 178 of the second wedge member 24 slide along the ramp surfaces 44 and 144, so as to separate the superior plate 18 from the inferior plate 20 along the vertical direction V. The ridges 182a-182d slide along respective inclined connection grooves 60a, 160a, 62a, 162a (not shown in the FIG. 7B). The flange 28 remains disposed in the slots 52, 54, 152, 154 during actuation of the implant 10 and provides additional stability against sheer when the implant 10 is expanded. The embodiment shown in FIGS. 7A and 7B illustrate the superior plate 18 separating from the inferior plate 20 along a vertical direction V while remaining generally parallel to each other. In other alternate embodiments, the implant can be configured to such that a lordotic or kyphotic distraction is achieved. For example, the threaded portions of the actuation member can be configured to cause one wedge member to translate at a faster rate compared to the other wedge member. In such an embodiment, when the implant 10 is expanded, the superior plate 18 will be angularly offset from the inferior plate 20.

Referring to FIGS. 9-11B, in accordance with, the alternative embodiment implant 110, the superior and interior plates 18 and 20, and specifically the interior include opposing depressions 49, 149 extending from the lumens 30, 131, toward the opposing ends 12, 14 of the implant. The first and second members 222 and 224 may include projecting tabs 120, 121, 122, and 123 (tab 121 not shown) protrude from the inclined surfaces 277 and 278 of the first and second wedge members 222 and 224. Further, the actuation member 226 can have a shorter length compared to actuation member 26 described above. Otherwise, the implant 110 shown in FIGS. 9-11B is similarly configured to implant 10.

Referring the FIGS. 10A-10C, the depressions 79 include a first 49A and a second depression 49B extending from the first and second ramp surfaces 44 and 46 along the vertical direction V. The depressions 49A, 49B define a shoulders 51a, 51b, 53a, 53b, against which a portion the wedge members 222 and 224 shoulder against when the implant is expanded.

Another aspect of the present disclosure is a method of inserting and expanding for inserting an expandable implant into an intervertebral space. The patient the intervertebral space 9 is prepared using familiar techniques. One or more trial implants may be used to determine the appropriate size of the implant 10. Using the tool 100 (FIG. 8A), the expandable implant can be clasped between the tabs 101 and 102. Next, the expandable implant 10 is inserted into the intervertebral space 9 at the appropriate position between the vertebral bodies using a unilateral and/or bilateral posterior approach or an anterior approach. Next, a tool 350 having configured to engage the opening 90 the actuation member 26 can be used to actuate. Rotating the tool 350 and actuation member 26 causes the actuating member 26 to separate the opposed wedge members 22 and 24 along the longitudinal direction L simultaneously, thereby causing the first plate to separate from the second plate along the second direction such that the first plate is parallel to the second plate during the expanding step.

In accordance with an alternative embodiment, the method of insertion and expansion can use a tool 300 shown in FIG. 8C-8F. For instance, the tool 300 can clasp the implant 10 by inserting the tool tabs 312 and 314 into the implant indentations 98 and 99. The rotation member 318 can be slid into engagement with the actuation member 26. The tool 300 can be used to insert the implant into the intervertebral space 9. When the implant 10 is in the appropriate position, the rotation member 318 can be rotated, which rotates the actuation member 26 such that the implant is expanded to the desired expansion height.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. An expandable implant for insertion in an intervertebral space defined between a first vertebral body and a second vertebral body, the implant defining an insertion end spaced apart from a trailing end along a longitudinal direction, the implant comprising:
   a first plate defining a first connection groove and a first projection;
   a second plate opposed to the first plate along a vertical direction that is perpendicular to the longitudinal direction, the second plate defining a second connection groove and a second projection, wherein the first and second projections are positioned between the first and second connection grooves with respect to the vertical direction;
   a first wedge member and a second wedge member spaced from the first wedge member along the longitudinal direction, each wedge member defining:
      an inner end and a narrow end spaced apart from the inner end along the longitudinal direction, each wedge member tapering from the inner end to the narrow end, the inner ends of each wedge member facing one another;
      a first side surface and a second side surface spaced from the first side surface along a transverse direction that is perpendicular to the longitudinal and vertical directions;
      a first ridge and a second ridge spaced from the first ridge with respect to the vertical direction, each of the first and second ridges 1) elongated in a direction extending from the narrow end to the inner end of the associated wedge member, and 2) protruding from one of the first and second side surfaces of the associated wedge member in the transverse direction,
      wherein the first ridge is received within the first connection groove and overlaps the first projection in the transverse direction so as to interlock the associated wedge member with the first plate, the second ridge is received within the second connection groove and overlaps the second projection in the transverse direction so as to interlock the associated wedge member with the second plate, and the first and second wedge members are configured to translate away from one another along the longitudinal direction along the first and second plates from a first contracted configuration of the first and second wedge members into a second separated configuration of the first and second wedge members; and
   an actuation member coupled to the first wedge member and the second wedge member, the actuation member defining a shaft having a proximal end and a distal end spaced from the proximal end along the longitudinal direction, the shaft defining a first threaded portion and a second threaded portion proximal to the first threaded portion, the actuation member defining a flange extending toward the first and second plates, the flange disposed between the first and second threaded portions, the actuation member configured to translate the first and second wedge members from the first contracted configuration into the second separated configuration so as to separate the first plate from the second plate along the vertical direction.

2. The implant of claim 1, wherein the first threaded portion has a first thread direction, and a second threaded portion has a second thread direction that is different than the first thread direction.

3. The implant of claim 2, wherein the first wedge member includes a first bore extending along the first direction between the narrow end and the inner end of the first wedge member, and the second wedge member includes a second bore extending along the first direction between the narrow end and the inner end of the second wedge member, wherein the first bore at least partially receives the first threaded portion of the actuation member, and the second bore at least partially receives the second threaded portion of the actuation member.

4. The implant of claim 1, wherein the first plate defines a first proximal ramp inclined toward the trailing end of the implant, and the second plate defines a second proximal ramp inclined toward the trailing end of the implant, wherein either of the first or second wedge member is configured to translate along the first and second proximal ramp toward the trailing end of the implant.

5. The implant of claim 4, wherein first plate defines a first distal ramp inclined toward the insertion end of the implant, and the second plate defines a second distal ramp inclined toward either of the insertion end of the implant, wherein the other of the first or second wedge member is configured to translate along the first and second distal ramp toward the insertion end of the implant.

6. The implant of claim 1, wherein each wedge member defines a body having a first inclined surface angularly offset from a second inclined surface, wherein the first and second inclined surfaces extend from the inner end toward the narrow end.

7. The implant of claim 6, wherein the first ridge extends along the first inclined surface, the second ridge extends along the second inclined surface, and the first and second ridges are configured to slidably couple with the first and second plates, respectively.

8. The implant of claim 6, wherein the first inclined surface defines a top surface of the associated wedge member, the second inclined surface defines a bottom surface of the associated wedge member, the first ridge is contiguous with the first inclined surface, and the second ridge is contiguous with the second inclined surface.

9. The implant of claim 1, wherein the implant is configured to expand from a collapsed configuration into an expanded configuration, the expanded configuration is defined as when the first plate is spaced apart from the second plate along the vertical direction, and when the implant is in the collapsed configuration, the inner ends of each wedge member abut the flange.

10. The implant claim 9, wherein the first plate defines a first lumen and the second plate defines a second lumen aligned with the first lumen, wherein when the implant is in the collapsed configuration, at least a portion of the first wedge member and the second wedge member is at least partially disposed in the first lumen and the second lumen.

11. The implant of claim 10, wherein the inner end of each wedge member includes a superior tip and an inferior tip spaced apart from the superior tip along the vertical direction, wherein when the implant is in the collapsed configuration, the superior tip extends into the first lumen and is at least aligned with a first bone contacting surface of the first plate, and the inferior tip extends into the second lumen and is at least aligned with a second bone contacting surface of the second plate.

12. The implant of claim 1, wherein the inner ends of the first and second wedge members are spaced apart to at least partially define a gap extending therebetween, and the flange is configured to extend through the gap and at least partially into the first and second plates.

13. The implant of claim 12, wherein when the first wedge member and the second wedge member separate from the first contracted configuration into the second separated configuration, the dimension of the gap is increased.

14. The implant of claim 1, wherein the first and second connection grooves and the first and second ridges are each sloped with respect to the longitudinal direction.

15. The implant of claim 14, wherein the first and second ridges are configured to ride along the first and second connection grooves, respectively, responsive to translation of the associated wedge member from the first contracted configuration to the second separated configuration so as to separate the first plate from the second plate along the vertical direction.

16. The implant of claim 1, wherein each wedge member further comprises a third ridge and a fourth ridge spaced from the third ridge with respect to the vertical direction, wherein,
    the third ridge protrudes, in the transverse direction, from the other of the first and second side surface of the associated wedge member from which the first ridge protrudes;
    the fourth ridge protrudes, in the transverse direction, from the other of the first and second side surfaces of the associated wedge member from which the second ridge protrudes; and
    each of the third and fourth ridges is elongated in a direction extending from the narrow end to the inner end of the associated wedge member.

17. The implant of claim 16, wherein the first and third ridges are parallel with each other, and the second and fourth ridges are parallel with each other.

18. The implant of claim 1, wherein:
    the first wedge member defines a first threaded feature coupled to the first threaded portion of the shaft;
    the second wedge member defines a second threaded feature coupled to the second threaded portion of the shaft; and
    the actuation member is configured to translate the first and second wedge members from the first contracted configuration into the second separated configuration responsive to rotation of the shaft about the central axis; and
    the first and second threaded portions of the shaft have different thread pitches so as to cause the first and second wedge members to translate at different rates responsive to rotation of the shaft in a manner causing the first and second plates to be separated by a first distance in the vertical direction at the insertion end and by a second distance in the vertical direction at the trailing end, and the first distance is different than the second distance.

19. An implant for insertion in an intervertebral space defined between a first vertebral body and a second vertebral body, the implant defining an insertion end spaced apart from an trailing end along a first direction, the implant comprising:
    a first plate defining a first connection groove and a first projection;

a second plate opposing the first plate along a second direction that is perpendicular to the first direction, the second plate defining a second connection groove and a second projection, wherein the first and second projections are positioned between the first and second connection grooves with respect to the second direction;

a first wedge member and a second wedge member spaced apart from the first wedge member along the first direction so as to define at least a gap between the first and second wedge members, each wedge member defining:
- a first end and a second end spaced from the first end along the first direction, the first ends of each wedge member facing one another so as to define a gap therebetween;
- a first side surface and a second side surface spaced from the first side surface along a third direction that is perpendicular to the first and second directions;
- a first ridge and a second ridge spaced from the first ridge with respect to the second direction, each of the first and second ridges 1) elongated in a direction extending from the first end to the second end of the associated wedge member, and 2) protruding from one of the first and second side surfaces of the associated wedge member in the third direction,
- wherein the first ridge is received within the first connection groove and overlaps the first projection in the third direction so as to interlock the associated wedge member to the first plate, the second ridge is received within the second groove and overlaps the second projection in the third direction so as to interlock the associated wedge member to the second plate, and the first wedge member and the second wedge member are translatable along the first and second plates along the first direction;

an actuation member defining a shaft having a first threaded portion coupled to the first wedge member and a second threaded portion spaced from the first threaded portion along the first direction, the second threaded portion coupled to the second wedge member; and a flange extending radially from the actuation member at least partially into the gap and at least partially into the first and second plates, the flange disposed between the first and second threaded portions of the shaft, wherein, when the actuation member is actuated, the first wedge member and the second wedge member separate from each other along the first direction so as to separate the first plate from the second plate along the second direction.

20. The implant of claim 19, further comprising a first lumen extending through the first plate, and a second lumen extending through the second plate and axially aligned with the first lumen.

21. The implant of claim 20, wherein the first plate defines a bone contacting surface and an inner surface opposed to the bone contacting surface, the inner surface defining a first ramp that extends from the first lumen toward the first end of the first plate, and a second ramp extending from the first lumen toward the second end of the first plate, wherein the first and second ramps slidingly mate with the respective first and second first wedge members.

22. The implant of claim 21, wherein at least the first ramp defines an elongate depression, wherein the elongate depression is configured to receive a tab extending from either of the first wedge member or the second wedge member along the second direction, wherein the tab is configured to abut a portion of the depression so as to limit advancement of the first and second wedge members relative to the first plate.

23. The implant of claim 21, wherein the second plate defines a second bone contacting surface and an inner surface opposed to the second bone contacting surface, the inner surface of the second plate defining a first ramp that extends from the second lumen toward the first end of the second plate, and a second ramp extending from the second lumen toward the second end of the second plate, wherein the first and second ramps slidingly mate with the respective first and second first wedge members.

24. The implant of claim 19, wherein the first plate defines a first bone contacting surface extending between the trailing end and the insertion end, and a first pair of opposed walls extending from the first bone contacting surface along the second direction, and the second plate defines a second bone contacting surface extending between the trailing end and the insertion end, the second bone contacting surface spaced from the first bone contacting surface along the second direction, and the second bone plate defines a second pair of opposed walls extending from the second bone contacting surface along the second direction toward the first plate, wherein the first and second pair of opposed walls each at least partially define a cavity configured to support the first and second wedge members.

25. The implant of claim 24, wherein one of the first pair of opposed walls defines at least one slot disposed between the insertion end and the trailing end, wherein the at least one slot is configured to receive a portion of the flange.

26. The implant of claim 24, wherein the first pair of opposed walls each define a first and second opposing slot, and the second pair of opposed second walls define a third and fourth opposing slot, wherein the first, second, third, and fourth opposing slots are disposed between the insertion end and the trailing end of the implant, and each slot is configured to receive a portion of the flange.

27. The implant of claim 24, wherein at least one wall of the first or second pair of opposed walls defines the first connection groove and the first projection, and the first connection groove is recessed into the at least one wall along the third direction.

* * * * *